United States Patent [19]
Kulagowski et al.

[11] Patent Number: 5,559,125
[45] Date of Patent: Sep. 24, 1996

[54] HYDROXYQUINOLONE DERIVATIVES

[75] Inventors: Janusz J. Kulagowski, Bishops Stortford; Paul D. Leeson, Cambridge; Ian M. Mawer, Bishops Stortford; Michael Rowley, Harlow, all of England

[73] Assignee: Merck, Sharp & Dohme Limited, Hoddesdon, England

[21] Appl. No.: 273,525

[22] Filed: Jul. 11, 1994

Related U.S. Application Data

[62] Division of Ser. No. 154,141, Nov. 18, 1993, Pat. No. 5,348,962.

[30] Foreign Application Priority Data

Oct. 19, 1990 [GB] United Kingdom ................... 9022785

[51] Int. Cl.$^6$ ........................ C07D 215/48; A61K 31/47
[52] U.S. Cl. ...................... 514/312; 514/235.2; 514/253; 546/155; 544/128; 544/363
[58] Field of Search ................................ 544/128, 363; 546/155; 514/235.2, 312, 253

[56] References Cited

U.S. PATENT DOCUMENTS 5,348,962  9/1994  Kulagowski et al. ................... 514/312

FOREIGN PATENT DOCUMENTS

| | | | |
|---|---|---|---|
| 0093521 | 11/1983 | European Pat. Off. | 546/155 |
| 0293146 | 11/1988 | European Pat. Off. | 546/155 |
| 0303387 | 2/1989 | European Pat. Off. | 546/155 |
| 0420806 | 9/1989 | European Pat. Off. | 546/155 |
| 0432994 | 6/1991 | European Pat. Off. | 546/155 |
| 63-295561 | 9/1987 | Japan | 546/312 |
| 1242585 | 9/1987 | Japan | 546/312 |

OTHER PUBLICATIONS

Dickenson and Aydar, "Antagonism at the glycine site on the NMDA receptor reduces spinal nociception in the rat", Neuroscience Letters, 121, 263–266 (1991).

Murray et al., "Neurokinin and NMDA antagonists (but not a kainic acid antagonist) are antinociceptive in the mouse formalin model", Pain, 44, 179–185 (1991).

Woolf and Thompson, "The induction and maintenance of central sensitization is dependent on N–methyl–D–aspartic acid receptor activation; implications for the treatment of post–injury pain hypersensitivity states", Pain, 44, 293–299 (1991).

Trullas and Skolnick, "Functional antagonists at the NMDA receptor complex exhibit antidepressant actions", European Journal of Pharmacology, 185, 1–10 (1990).

Kehne, et al., "NMDA receptor complex antagonists have potential anxiolytic effects as measured with separation–induced ultrasonic vocalizations", European Journal of Pharmacology, 193, 283–292 (1990).

Werling, et al., "Regulation of [3H] Dopamine Release from Guinea Pig Striatum by NMDA Receptor/Channel Activators and Inhibitors1", The Journal of Pharmacology and Experimental Therapeutics, 255, 1, 40–45 (1990).

Graham, et al., "Atypical Endogenous Opioid Systems in Mice in Relation to an Auto–Addiction Opioid Model of Anorexia Nervosa", Life Sciences, 47, 16, 1427–1435 (1990).

Turski, et al., "Protection of substantia nigra from MPP+ neurotoxicity by N–methyl–D–aspartate antagonists", Nature, 349, 414–418 (1991).

Lauritzen, et al., "XV–4. The Neuroprotective Effect on the NMDA Antagonist MK801 and Non–NMDA Antagonist NBQX is not Explained by an Effect on Anoxic Depolarization, and only MK801 Inhibits Spreading Depression", Journal of Cerebral Blood Flow and Metabolism, II, 2, Abstract S222 (1991).

Bagetta, et al., "Prevention by the NMDA receptor antagonist, MK801 of neuronal loss produced by tetanus toxin in the rat hippocampus", British Journal Pharmacology, 101, 776–780 (1990).

Lipton, et al., "AIDS Virus Coat Protein Sensitizes Neurons to NMDA Receptor–Mediated Toxicity", Society for Neuroscience Abstracts, 16, 1, 128.11 (1990).

van den Pol, et al., "Glutamate, the Dominant Excitatory Transmitter in Neuroendocrine Regulation", Science, 250, 1276–1278 (1990).

Urbanski, "A Role for N–Methyl–D–Aspartate Receptors in the Control of Seasonal Breeding", Endocrinology, 127, 5, 2223–2228 (1990).

Christie, et al., "An Excitant Amino Acid Projection from the Medial Prefrontal Cortex to the Anterior Part of Nucleus Accumbens in the Rat", Journal of Neurochemistry, 45, 2, 477–482 (1985).

Rudolph, et al., "L–Glutamic Acid, A Neuromodulator of Dopaminergic Transmission in the Rat Corpus Striatum", Neurochemistry International, 5, 479–486 (1983).

Arnt, "Hyperactivity Following Injection of a Glutamate Agonist and 6,7–ADTN into Rat Nucleus Accumbens and its Inhibition by THIP", Life Sciences, 28, 14, 1597–1603 (1981).

Yamaguchi, et al., "The Synthesis of Benzofuroquinolines, III. Two Dihydroxybenzofuroquinolinones", Journal of Heterocycl. Chemistry, 21, 737–739 (1984).

Nishimura, et al., "Synthesis of 4–Hydroxy–2(1H)–quinolone Derivatives", Yakugaku Zasshi, 90, 818–828 (1970) (English Translation).

Stadlbauer and Kappe, "Oxidative Hydroxylation of Heterocyclic B–Dicarbonyl Compounds", Monatshefte fur Chemie, 116, 1005–1015 (1985) (English Translation).

(List continued on next page.)

*Primary Examiner*—Zinna Northington Davis
*Attorney, Agent, or Firm*—Robert J. North; Melvin Winokur

[57] ABSTRACT

A class of 4-hydroxy-2-(1H)-quinolone derivatives, substituted at the 3-position by an optionally substituted aryl substituent, are selective non-competitive antagonists of NMDA receptors and/or are antagonists of AMPA receptors, and are therefore of utility in the treatment of conditions, such as neurodegenerative disorders, convulsions or schizophrenia, which require the administration of an NMDA and/or AMPA receptor antagonist.

13 Claims, No Drawings

OTHER PUBLICATIONS

Kappe, et al., "Syntheses of Heterocycles, 131st Report: On the Reactions of Some Mesoxalyl Heterocycles and their Animals", Monatshefte fur Chemie, 100, 951–959 (1969) (English Translation).

Sterk and Ziegler, "Infrared Spectroscopic Studies of 4–hydroxycarbostyril and its Derivatives", Monatshefte fur Chemie, 98, 100–104 (1967) (English Translation).

Kawase, et al., "The Synthesis of Benzofuroquinolines. II. Two Benzofuroquinolinones and Some Benzofuroquinoline Derivatives", Bulletin Chemical Society. Japan, 53, 1057–1060 (1980).

Yamaguchi, et al., "The Synthesis of Benzofuroquinolines. IV. Some Halobenzofuro[2,3–b]–and [3,2–c]quinoline Derivatives", J. Heterocyclic Chemistry, 26, 281–284 (1989).

Walser, et al., "Nucleophilic Displacement of Aromatic Fluorine, Part III (1), Indoloquinolines and Benzofuranoquinolines", J. Heterocyclic Chemistry, 12, 351–358 (1975).

Kappe, et al., "Synthesis of Benzo–halogenated 4–Hydroxy–2((1H) quinolones", J. Heterocyclic Chemistry, 25, 857–862 (1988).

Stadlbauer and Kappe, "Syntheses of 3–Hydroxy–tetrahydroquinoline–2,4–diones)", Z. Naturforsch. 37b, 1196–1200 (1982) (English Translation).

Diesbach, et al., "128. On Some Derivatives of the Phenyl–hydroxy–quinolines", Helvetica Chimica Acta., 34, 1050–1060 (1951) (English Translation).

Grimwood, et al., "204P Modulation by Polyamines of [3H]L–689,560 Binding to the Glycine Site on the N–Methyl–D–Aspartate Receptor from Rat Cortex/Hippocampus Membranes", British Journal of Pharmacology Proceedings Supplement, 107, 204P (1992).

Wong, et al., "The anticonvulsant MK–801 is a potent N–methyl–D–aspartate antagonist", Proc Natl. Acad. Sci. U.S.A., 83, 7104–7108 (1986).

HYDROXYQUINOLONE DERIVATIVES

This is a division of application Ser. No. 08/154,141 filed Nov. 18, 1993, now U.S. Pat. No. 5,348,962.

This invention relates to a class of 4-hydroxy-2(1H)-quinolones which are substituted in the 3-position by an optionally substituted aryl substituent. These compounds are selective non-competitive antagonists of N-methyl-D-aspartate (NMDA) receptors. More particularly, the class of compounds provided by the present invention are ligands for the strychnine-insensitive glycine modulatory site of the NMDA receptor and are therefore useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-pontocerebellar atrophy, anoxia such as from drowning, spinal cord and head injury, and poisoning by exogenous and endogenous NMDA receptor agonists and neurotoxins, including environmental neurotoxins.

By virtue of their NMDA receptor antagonist properties, the compounds according to the present invention are also useful as anticonvulsant and antiemetic agents, as well as being of value in the prevention or reduction of dependence on dependence-inducing agents such as narcotics.

NMDA receptor antagonists have recently been shown to possess analgesic (see, for example, Dickenson and Aydar, *Neuroscience Lett.*, 1991, 121, 263; Murray et al., *Pain*, 1991, 44, 179; and Woolf and Thompson, *Pain*, 1991, 44, 293), antidepressant (see, for example, Trullas and Skolnick, *Eur. J. Pharmacol.*, 1990, 185, 1) and anxiolytic (see, for example, Kehne et al., *Eur. J. Pharmacol.*, 1991, 193, 283) effects, and the compounds of the present invention may accordingly be useful in the management of pain, depression and anxiety.

The association of NMDA receptor antagonists with regulation of the nigrostriatal dopaminergic system has recently been reported (see, for example, Werling et al., *J. Pharmacol. Ext. Ther.*, 1990, 255, 40; Graham et al., *Life Sciences*, 1990, 47, PL-41; and Turski et al., *Nature (London)*, 1991, 349, 414). This suggests that the compounds of the present invention may thus be of assistance in the prevention and/or treatment of disorders of the dopaminergic system such as schizophrenia and Parkinson's disease.

It has also been reported recently (see Lauritzen et al., *Journal of Cerebral Blood Flow and Metabolism*, 1991, vol. 11, suppl. 2, Abstract XV-4) that NMDA receptor antagonists block cortical spreading depression (CSD), which may thus be of clinical importance since CSD is a possible mechanism of migraine. The class of substituted 2-amino-4-phosphonomethylalk-3-ene carboxylic acids and esters described in EP-A-0420806, which are stated to be selective NMDA antagonists, are alleged thereby to be of potential utility in the treatment of inter alia migraine.

Excitatory amino acid receptor antagonists, including inter alia antagonists of NMDA receptors, are alleged in EP-A-0432994 to be of use in suppressing emesis.

Recent reports in the literature have also suggested a link between the neurotoxicity of certain viruses and the deleterious effects of these viruses on an organism caused by the potentiation of neurotransmission via excitatory amino acid receptors. By virtue of their activity as antagonists of NMDA receptors, therefore, the compounds of the present invention may be effective in controlling the manifestations of neuroviral diseases such as measles, rabies, tetanus (cf. Bagetta et al., *Br. J. Pharmacol.*, 1990, 101, 776) and AIDS (cf. Lipton et al., *Society for Neuroscience Abstracts*, 1990, 16, 128.11).

NMDA antagonists have, moreover, been shown to have an effect on the neuroendocrine system (see, for example, van den Pol et al., *Science*, 1990, 250, 1276; and Urbanski, *Endocrinology*, 1990, 127, 2223), and the compounds of this invention may therefore also be effective in the control of seasonal breeding in mammals.

In addition, certain compounds of the invention are antagonists of 2-amino-3-hydroxy-5-methyl-4-isoxazolepropionic acid (AMPA) receptors, also known as quisqualate receptors. An excitatory amino acid projection from the prefrontal cortex to the nucleus accumbens (a particular region of the forebrain possessing dopamine-sensitive neurones) is well known to exist (see, for example, *J. Neurochem.*, 1985, 45, 477). It is also well known that dopaminergic transmission in the striatum is modulated by glutamate (see, for example, *Neurochem. Int.*, 1983, 5, 479), as also is the hyperactivity associated with presynaptic stimulation of the dopamine system by AMPA in the nucleus accumbens (cf. *Life Sci.*, 1981, 28, 1597). Compounds which are antagonists of AMPA receptors are therefore of value as neuroleptic agents.

A class of 4-hydroxy-3-phenyl-2(1H)-quinolone derivatives, substituted at the 7-position by an unsubstituted straight or branched alkoxy group containing 2 to 10 carbon atoms or by a straight or branched alkoxy group containing 1 to 6 carbon atoms having at least one substituent selected from hydroxy, carboxy and carbamoyl, is described in JP-A-63-295561. These compounds are stated therein to exhibit a strong inhibitory action on bone resorption and a stimulatory effect on ossification, and thus to be useful as therapeutic agents for the prevention and treatment of osteoporosis.

EP-A-0293146 and JP-A-1-242585 describe a range of 4-hydroxy-3-phenyl-2(1H)-quinolones, which are substituted in a variety of positions by hydroxy or lower alkoxy substituents, as intermediates in the preparation of various benzofuro[3,2-c]quinoline derivatives. The latter compounds are also alleged to be useful agents for the prevention and treatment of osteoporosis.

A specific methoxylated 4-hydroxy-3-phenyl-2(1H)-quinolone derivative, namely 3-(2,4-dimethoxyphenyl)-4-hydroxy-7-methoxy-2(1H)-quinolone, is disclosed in *J. Heterocycl. Chem.*, 1984, 21, 737.

*Yakugaku Zasshi*, 1970, 90, 818 describes a range of 4-hydroxy-3-phenyl-2(1H)-quinolones optionally substituted at the 6-, 7- or 8-position by a number of different functional groups. In certain of these compounds, the 3-phenyl substituent is itself substituted at the ortho or para position by a methyl group.

Various 4-hydroxy-3-phenyl-2(1H)-quinolone derivatives, optionally mono- or disubstituted on the benzo moiety of the tetrahydroquinoline ring system, and optionally monosubstituted at the ortho or para position of the 3-phenyl substituent by various groups, are disclosed in EP-A-0093521; *Monatsh. Chem.*, 1985, 116, 1005; *Monatsh. Chem.*, 1969, 100, 951; *Monatsh. Chem.*, 1967, 98, 100; *Bull. Chem. Soc. Jpn.*, 1980, 53, 1057; *J. Heterocycl. Chem.*, 1989, 26, 281; *J. Heterocycl. Chem.*, 1988, 25, 857; *J. Heterocycl. Chem.*, 1975, 12, 351; *Z. Naturforsch.*, 1982, 37b, 1196; and *Helv. Chim. Acta*, 1951, 34, 1050.

Except for JP-A-63-295561 as mentioned above, none of the aforementioned publications discloses any therapeutic utility for the various 4-hydroxy-3-phenyl-2(1H)-quinolone derivatives described therein. Moreover, in none of the prior art documents is there any suggestion that the compounds described therein would be of assistance in solving the problem of providing an effective agent for the treatment and/or prevention of conditions requiring the administration of an antagonist of NMDA and/or AMPA receptors.

The present invention accordingly provides the use of a compound of formula I or a pharmaceutically acceptable salt thereof or a prodrug thereof:

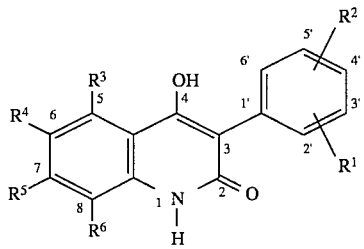

wherein $R^1$ and $R^2$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; or $R^1$ and $R^2$ together represent the residue of a carbocyclic or heterocyclic ring;

$R^3$, $R^4$, $R^5$ and $R^6$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group; for the manufacture of a medicament for the treatment and/or prevention of conditions, in particular neurodegenerative disorders, which require the administration of a selective non-competitive antagonist of NMDA receptors.

The present invention further provides the use of a compound of formula I as defined above or a pharmaceutically acceptable salt thereof or a prodrug thereof for the manufacture of a medicament for the treatment and/or prevention of conditions, such as schizophrenia, which require the administration of an antagonist of AMPA receptors.

The compound of formula I will in general exist in equilibrium with its other tautomeric forms, including those structures of formulae A to D:

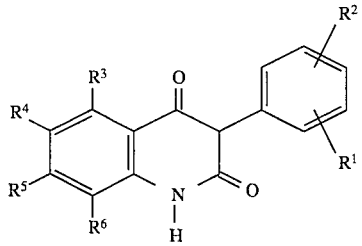

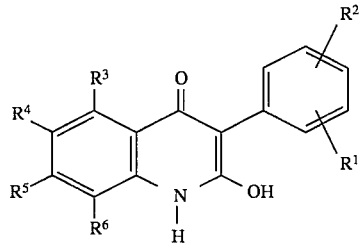

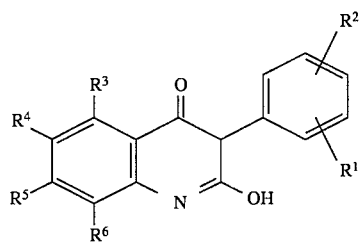

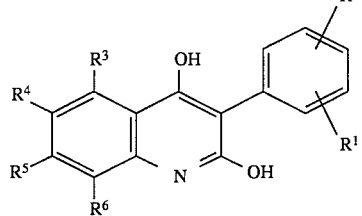

wherein $R^1$ to $R^6$ are as defined with reference to formula I above. Indeed, in the prior art references cited above, the compounds disclosed therein are variously designated by reference to one or other of these tautomeric forms. It is to be understood that all tautomeric forms of the compounds of formula I, as well as all possible mixtures thereof, are included within the scope of the present invention.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl ($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups.

A particular aryl($C_{1-6}$)alkyl group is benzyl.

A particular aryl($C_{2-6}$)alkenyl group is phenylethenyl.

A particular aryl($C_{2-6}$)alkynyl group is phenylethynyl.

Suitable heterocycloalkyl groups include piperidyl, piperazinyl and morpholinyl groups.

A particular heterocycloalkyl($C_{1-6}$)alkyl group is morpholinylethyl.

Suitable heteroaryl groups include pyridyl, quinolyl, isoquinolyl, pyridazinyl, pyrimidinyl, pyrazinyl, pyrrolyl, indolyl, pyranyl, furyl, benzofuryl, thienyl, benzthienyl, imidazolyl, oxadiazolyl and thiadiazolyl groups. Particular heteroaryl groups are pyridyl, pyrrolyl, indolyl, furyl, benzofuryl, thienyl, benzthienyl and oxadiazolyl.

Particular heteroaryl($C_{1-6}$)alkyl groups include pyridylmethyl, pyrrolylmethyl, indolylmethyl, furylmethyl and thienylmethyl.

Where $R^1$ and $R^2$ together represent the residue of a carbocyclic or heterocyclic ring, the ring may be saturated or unsaturated. The ring may suitably be a 4- to 9-membered ring, but will preferably be a 5- or 6-membered ring. Where $R^1$ and $R^2$ together represent the residue of a heterocyclic ring, this ring may contain up to four heteroatoms selected from oxygen, nitrogen and sulphur. Suitable carbocyclic rings of which $R^1$ and $R^2$ together represent the residue include cyclohexane, cyclohexene, cyclohexadiene and benzene rings. Suitable heterocyclic rings of which $R^1$ and $R^2$ together represent the residue include dioxolane, dioxane, pyridine, furan, thiophene, pyrrole, thiazole and thiadiazole rings.

The hydrocarbon and heterocyclic groups, as well as the carbocyclic or heterocyclic ring completed by $R^1$ and $R^2$, may in turn be optionally substituted by one or more groups selected from $C_{1-6}$ alkyl, adamantyl, phenyl, halogen, $C_{1-6}$ haloalkyl, morpholinyl($C_{1-6}$)alkyl, trifluoromethyl, hydroxy, $C_{1-6}$ alkoxy, $C_{1-6}$ alkoxy($C_{1-6}$)alkyl, $C_{1-6}$ alkoxy($C_{1-6}$)alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, amino, mono- or di($C_{1-6}$)alkylamino, $C_{2-6}$ alkylcarbonylamino and $C_{2-6}$ alkoxycarbonylamino.

The term "halogen" as used herein includes fluorine, chlorine, bromine and iodine, especially chlorine.

Suitable values for the substituents $R^1$ and $R^2$ include $C_{1-6}$ alkyl, aryl, aryl($C_{1-6}$)alkyl, aryl($C_{2-6}$)alkenyl, aryl($C_{2-6}$)alkynyl, heteroaryl($C_{1-6}$)alkyl, $C_{1-6}$ alkoxy, $C_{2-6}$ alkenyloxy, aryloxy, aryl($C_{1-6}$)alkoxy, heteroaryloxy, arylthio, arylsulphonyl, arylamino, aryl($C_{1-6}$)alkylamino, di($C_{1-6}$)alkylamino, arylcarbonylamino, arylcarbonyl or heteroarylcarbonyl, any of which groups may be optionally substituted; and hydrogen, halogen, trifluoromethyl or nitro. Examples of optional substituents on the groups $R^1$ and/or $R^2$ include $C_{1-6}$ alkyl, morpholinyl($C_{1-6}$)alkyl, hydroxy, $C_{1-6}$ alkoxy, $C_{1-6}$ alkoxy($C_{1-6}$)alkyl, $C_{1-6}$ alkoxy($C_{1-6}$)alkoxy, $C_{1-6}$ alkylthio and di($C_{1-6}$)alkylamino.

Particular values for the substituents $R^1$ and $R^2$ include hydrogen, methyl, phenyl, benzyl, methoxymethylbenzyl, morpholinylethyl-benzyl, hydroxybenzyl, methoxybenzyl, methoxymethoxy-benzyl, methylthio-benzyl, phenylethenyl, phenylethynyl, thienylmethyl, pyrrolylmethyl, indolylmethyl, fluoro, chloro, bromo, iodo, trifluoromethyl, nitro, methoxy, ethoxy, allyloxy, methyl-allyloxy, phenoxy, methyl-phenoxy, methoxy-phenoxy, dimethylamino-phenoxy, benzyloxy, furyloxy, thienyloxy, pyridyloxy, phenylthio, phenylsulphonyl, phenylamino, benzylamino, dimethylamino, phenylcarbonylamino, phenylcarbonyl, furylcarbonyl and thienylcarbonyl.

Suitably, one of $R^1$ and $R^2$ represents hydrogen. Preferably, at least one of $R^1$ and $R^2$ is other than hydrogen.

Where $R^1$ and $R^2$ together represent the residue of a carbocyclic or heterocyclic ring, this may be, in particular, a dioxolane or optionally substituted benzene ring.

The benzo moiety of the 4-hydroxy-2(1H)quinolone ring system shown in formula I above may be substituted or unsubstituted. Particular substituents include halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio and $C_{2-7}$ alkoxycarbonyl. Suitably $R^6$ is hydrogen and $R^3$, $R^4$ and $R^5$ independently represent hydrogen, halogen, cyano, trifluoromethyl, nitro, $C_{1-6}$ alkyl or $C_{2-6}$ alkenyl, at least one of $R^3$, $R^4$ and $R^5$ desirably being other than hydrogen. Preferably, $R^4$ and $R^6$ each represents hydrogen and $R^3$ and $R^5$ independently represent hydrogen, cyano, trifluoromethyl, nitro, methyl, ethyl, vinyl or halogen, especially chlorine or iodine. In a particular embodiment, $R^5$ represents cyano, trifluoromethyl, nitro or halogen, especially chlorine; and $R^3$ is hydrogen or ethyl.

In a further aspect, the invention provides a pharmaceutical composition comprising a compound of formula IA or a pharmaceutically acceptable salt thereof or a prodrug thereof:

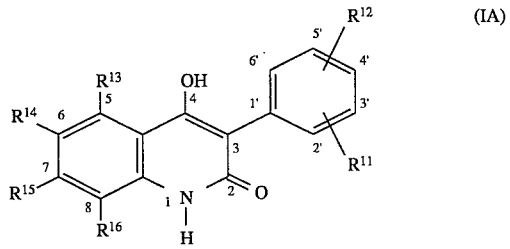

(IA)

wherein $R^{11}$ and $R^{12}$ independently represent hydrogen, hydrocarbon, a heterocyclic group, halogen, cyano, trifluoromethyl, nitro, $-OR^a$, $-SR^a$, $-SOR^a$, $-SO_2R^a$, $-SO_2NR^aR^b$, $-NR^aR^b$, $-NR^aCOR^b$, $-NR^aC_2R^b$, $-COR^a$, $-CO_2R^a$ or $-CONR^aR^b$; or $R^{11}$ and $R^{12}$ together represent the residue of a carbocyclic or heterocyclic ring;

$R^{13}$, $R^{14}$, $R^{15}$ and $R^{16}$ independently represent hydrogen, hydrocarbon, a heterocyclic group, halogen, cyano, trifluoromethyl, nitro, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$, or $-CONR^aR^b$; and $R^a$ and $R^b$ independently represent hydrogen, hydrocarbon or a heterocyclic group;

provided that, when $R^{11}$, $R^{12}$, $R^{13}$, $R^{14}$ and $R^{16}$ each represents hydrogen, then $R^{15}$ does not represent an unsubstituted straight or branched alkoxy group containing 2 to 10 carbon atoms or a straight or branched alkoxy group containing 1 to 6 carbon atoms having at least one substituent selected from hydroxy, carboxy and carbamoyl;

in association with one or more pharmaceutically acceptable carriers and/or excipients.

The invention also provides a compound of formula IA as defined above or a pharmaceutically acceptable salt thereof or a prodrug thereof for use in therapy.

Subject to the above proviso, the substituents $R^{11}$ to $R^{16}$ in the compounds of formula IA correspond to the substituents $R^1$ to $R^6$ respectively as defined with reference to the compounds of formula I.

Particular pharmaceutical compositions according to the invention contain, as the active ingredient, at least one of the following compounds:

4-hydroxy-3-phenyl-2(1H)-quinolone;

7-chloro-4-hydroxy-3-phenyl-2(1H)-quinolone;

7-chloro-4-hydroxy-3-(2-methylphenyl)-2(1H)-quinolone;

7-chloro-4-hydroxy-3-(4-methylphenyl)-2(1H)-quinolone;

4-hydroxy-3-phenyl-7-trifluoromethyl-2(1H)-quinolone;

6,7-dichloro-4-hydroxy-3-phenyl-2(1H)-quinolone;

and pharmaceutically acceptable salts thereof and prodrugs thereof.

Certain compounds falling within the definition of formula I above are novel. Accordingly, in a still further aspect the present invention provides a compound of formula IB or a salt or prodrug thereof:

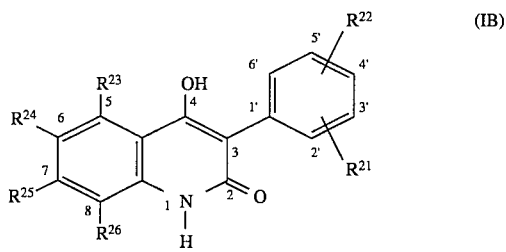

(IB)

wherein $R^{21}$ and $R^{22}$ independently represent hydrogen, hydrocarbon, a heterocyclic group, halogen, cyano, trifluoromethyl, nitro, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$ or $-CONR^aR^b$; or $R^{21}$ and $R^{22}$ together represent the residue of a carbocyclic or heterocyclic ring;

$R^{23}$, $R^{24}$, $R^{25}$ and $R^{26}$ independently represent hydrogen, hydrocarbon, a heterocyclic group, halogen, cyano, trifluoromethyl, nitro, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$ or $-CONR^aR^b$; and $R^a$ and $R^b$ independently represent hydrogen, hydrocarbon or a heterocyclic group;

provided that, when $R^{21}$ and $R^{22}$ each represents hydrogen, then:

(i) $R^{24}$ does not represent hydrogen, methyl, chloro, hydroxy, methoxy or acetoxy when $R^{23}$, $R^{25}$ and $R^{26}$ each represents hydrogen; and (ii) $R^{25}$ does not represent methyl, chloro, trifluoromethyl, hydroxy, benzoyloxy or an unsubstituted straight or branched alkoxy group containing 1 to 10 carbon atoms or a straight or branched alkoxy group containing 1 to 6 carbon atoms having at least one substituent selected from hydroxy, carboxy and carbamoyl when $R^{23}$, $R^{24}$ and $R^{26}$ each represents hydrogen; and (iii) $R^{26}$ does not represent methyl, phenyl, chloro or methoxy when $R^{23}$, $R^{24}$ and $R^{25}$ each represents hydrogen; and (iv) $R^{25}$ does not represent chloro when $R^{23}$ and $R^{24}$ each represents hydrogen and $R^{26}$ is methoxy, or when $R^{23}$ and $R^{26}$ each represents hydrogen and $R^{24}$ is chloro; and (v) $R^{26}$ does not represent chloro when $R^{23}$ and $R^{25}$ each represents hydrogen and $R^{24}$ is chloro, or when $R^{24}$ and $R^{25}$ each represents hydrogen and $R^{23}$ is chloro;

provided also that, when one of $R^{21}$ and $R^{22}$ represents hydroxy or lower alkoxy and the other represents hydrogen, hydroxy or lower alkoxy, and $R^{23}$, $R^{24}$ and $R^{26}$ each represents hydrogen, then $R^{25}$ does not represent hydroxy or lower alkoxy;

provided also that, when $R^{21}$ is 2'-methyl and $R^{22}$ is hydrogen, then:

(i) $R^{24}$ does not represent hydrogen, chloro or methoxy when $R^{23}$, $R^{25}$ and $R^{26}$ each represents hydrogen; and (ii) $R^{25}$ does not represent chloro or methoxy when $R^{23}$, $R^{24}$ and $R^{26}$ each represent hydrogen; and (iii) $R^{26}$ does not represent chloro when $R^{23}$, $R^{24}$ and $R^{25}$ each represents hydrogen;

provided also that, when $R^{21}$ and $R^{23}$ each represents hydrogen, one of the substituents $R^{24}$, $R^{25}$ and $R^{26}$ is chloro and the remainder represent hydrogen, then $R^{22}$ does not represent 4'-methyl;

provided also that, when $R^{21}$ is 2'-methoxy and $R^{22}$, $R^{23}$, $R^{25}$ and $R^{26}$ each represents hydrogen, then $R^{24}$ does not represent hydrogen, fluoro, chloro or bromo;

further provided that, when $R^{21}$, $R^{23}$, $R^{24}$, $R^{25}$ and $R^{26}$ each represents hydrogen, then $R^{22}$ does not represent 2'-fluoro, 2'-nitro, 2'-amino, 4'-chloro, 4'-hydroxy or 4'-methoxy.

Subject to the above provisos, the substituents $R^{21}$ to $R^{26}$ in the compounds of formula IB correspond to the substituents $R^1$ to $R^6$ respectively as defined with reference to the compounds of formula I.

For use in medicine, the salts of the compounds of formula IB will be non-toxic pharmaceutically acceptable salts. Other salts may, however, be useful in the preparation of the compounds according to the invention or of their non-toxic pharmaceutically acceptable salts.

Suitable pharmaceutically acceptable salts of the compounds of formulae I, IA and IB above include alkali metal salts, e.g. lithium, sodium or potassium salts; alkaline earth metal salts, e.g. calcium or magnesium salts; and salts formed with suitable organic ligands, e.g. quaternary ammonium salts. Where appropriate, acid addition salts may, for example, be formed by mixing a solution of the compound according to the invention with a solution of a pharmaceutically acceptable non-toxic acid such as hydrochloric acid, fumaric acid, maleic acid, succinic acid, acetic acid, citric acid, tartaric acid, carbonic acid or phosphoric acid.

The present invention includes within its scope prodrugs of the compounds of formulae I, IA and IB above. In general, such prodrugs will be functional derivatives of the compounds of formulae I, IA and IB which are readily convertible in vivo into the required compound. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

One sub-class of compounds according to the invention is represented by the compounds of formula IIA and salts and prodrugs thereof:

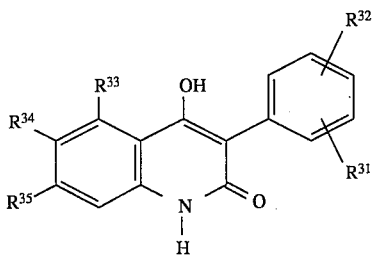 (IIA)

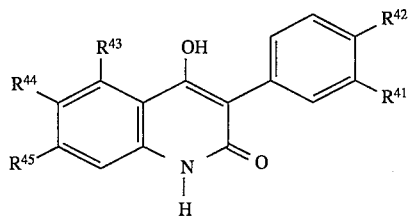 (IIB)

wherein $R^{31}$ and $R^{32}$ independently represent $C_{1-6}$ alkyl, $C_{2-6}$ alkenyl, $C_{2-6}$ alkynyl, aryl, aryl($C_{1-6}$)alkyl, aryl($C_{2-6}$)alkenyl, aryl($C_{2-6}$)alkynyl, heteroaryl($C_{1-6}$)alkyl, $C_{1-6}$ alkoxy, $C_{2-6}$ alkenyloxy, aryloxy, aryl($C_{1-6}$)alkoxy, heteroaryloxy, $C_{1-6}$ alkylthio, arylthio, arylsulphonyl, arylamino, aryl($C_{1-6}$)alkylamino, di($C_{1-6}$)alkylamino, arylcarbonylamino, arylcarbonyl, heteroarylcarbonyl or $C_{2-7}$ alkoxycarbonyl, any of which groups may be optionally substituted; or hydrogen, halogen, cyano, trifluoromethyl, nitro, hydroxy, amino or carboxy; or $R^{31}$ and $R^{32}$ together represent the residue of a carbocyclic or heterocyclic ring;

$R^{33}$ and $R^{35}$ independently represent halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl; and $R^{34}$ represents hydrogen or halogen.

Examples of optional substituents on the groups $R^{31}$ and/or $R^{32}$ include $C_{1-6}$ alkyl, morpholinyl($C_{1-6}$)alkyl, hydroxy, $C_{1-6}$ alkoxy, $C_{1-6}$ alkoxy($C_{1-6}$)alkyl, $C_{1-6}$ alkoxy($C_{1-6}$)alkoxy, $C_{1-6}$ alkylthio and di($C_{1-6}$)alkylamino.

Particular values of $R^{31}$ and/or $R^{32}$ with respect to formula IIA include hydrogen, methyl, phenyl, benzyl, methoxymethyl-benzyl, morpholinylethyl-benzyl, hydroxybenzyl, methoxybenzyl, methoxymethoxy-benzyl, methylthiobenzyl, phenylethenyl, phenylethynyl, thienylmethyl, pyrrolylmethyl, indolylmethyl, fluoro, chloro, bromo, iodo, trifluoromethyl, nitro, methoxy, ethoxy, allyloxy, methylallyloxy, phenoxy, methyl-phenoxy, methoxy-phenoxy, dimethylamino-phenoxy, benzyloxy, furyloxy, thienyloxy, pyridyloxy, phenylthio, phenylsulphonyl, phenylamino, benzylamino, dimethylamino, phenylcarbonylamino, phenylcarbonyl, furylcarbonyl and thienylcarbonyl.

Suitably, one of $R^{31}$ and $R^{32}$ represents hydrogen. Preferably, at least one of $R^{31}$ and $R^{32}$ is other than hydrogen. In an especial embodiment, one of $R^{31}$ and $R^{32}$ is hydrogen and the other is hydrogen or phenoxy.

Suitably, $R^{33}$ represents nitro, methyl, ethyl, vinyl or halogen, especially chlorine or iodine. Preferably, $R^{33}$ is ethyl or iodine.

Suitably, $R^{34}$ represents hydrogen or chlorine, preferably hydrogen.

Suitably, $R^{35}$ represents cyano, trifluoromethyl, nitro, methyl or halogen, preferably chlorine.

Another sub-class of compounds according to the invention is represented by the compounds of formula IIB and salts and prodrugs thereof:

wherein $R^{41}$ represents $C_{1-6}$ alkyl, $C_{2-6}$ alkenyl, $C_{2-6}$ alkynyl, aryl, aryl($C_{1-6}$)alkyl, aryl($C_{2-6}$)alkenyl, aryl($C_{2-6}$)alkynyl, heteroaryl($C_{1-6}$)alkyl, $C_{1-6}$ alkoxy, $C_{2-6}$ alkenyloxy, aryloxy, aryl($C_{1-6}$)alkoxy, heteroaryloxy, $C_{1-6}$ alkylthio, arylthio, arylsulphonyl, arylamino, aryl($C_{1-6}$)alkylamino, di($C_{1-6}$)alkylamino, arylcarbonylamino, arylcarbonyl, heteroarylcarbonyl or $C_{2-7}$ alkoxycarbonyl, any of which groups may be optionally substituted; or halogen, cyano, trifluoromethyl, nitro, hydroxy, amino or carboxy; and $R^{42}$ represents $C_{1-6}$ alkyl, $C_{2-6}$ alkenyl, $C_{2-6}$ alkynyl, aryl, aryl($C_{1-6}$)alkyl, aryl($C_{2-6}$)alkenyl, aryl($C_{2-6}$)alkynyl, heteroaryl($C_{1-6}$)alkyl, $C_{1-6}$ alkoxy, $C_{2-6}$ alkenyloxy, aryloxy, aryl($C_{1-6}$)alkoxy, heteroaryloxy, $C_{1-6}$ alkylthio, arylthio, arylsulphonyl, arylamino, aryl($C_{1-6}$)alkylamino, di($C_{1-6}$)alkylamino, arylcarbonylamino, arylcarbonyl, heteroarylcarbonyl or $C_{2-7}$ alkoxycarbonyl, any of which groups may be optionally substituted; or hydrogen, halogen, cyano, trifluoromethyl, nitro, hydroxy, amino or carboxy; or $R^{41}$ and $R^{42}$ together represent the residue of a carbocyclic or heterocyclic ring;

$R^{43}$ and $R^{44}$ independently represent hydrogen, halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl; and $R^{45}$ represents hydrogen, halogen, cyano, trifluoromethyl, nitro, hydroxy, amino, carboxy, $C_{1-6}$ alkyl, $C_{2-6}$ alkenyl, $C_{1-6}$ alkylthio or $C_{2-7}$ alkoxycarbonyl.

Examples of optional substituents on the groups $R^{41}$ and/or $R^{42}$ include $C_{1-6}$ alkyl, morpholinyl($C_{1-6}$)alkyl, hydroxy, $C_{1-6}$ alkoxy, $C_{1-6}$ alkoxy($C_{1-6}$)alkyl, $C_{1-6}$ alkoxy($C_{1-6}$)alkoxy, $C_{1-6}$ alkylthio and di($C_{1-6}$)alkylamino.

Particular values of $R^{41}$ and/or $R^{42}$ with respect to formula IIA include methyl, phenyl, benzyl, methoxymethyl-benzyl, morpholinylethyl-benzyl, hydroxybenzyl, methoxybenzyl, methoxymethoxy-benzyl, methylthio-benzyl, phenylethenyl, phenylethynyl, thienylmethyl, pyrrolylmethyl, indolylmethyl, fluoro, chloro, bromo, iodo, trifluoromethyl, nitro, methoxy, ethoxy, allyloxy, methyl-allyloxy, phenoxy, methylphenoxy, methoxy-phenoxy, dimethylamino-phenoxy, benzyloxy, furyloxy, thienyloxy, pyridyloxy, phenylthio, phenylsulphonyl, phenylamino, benzylamino, dimethylamino, phenylcarbonylamino, phenylcarbonyl, furylcarbonyl and thienylcarbonyl. $R^{42}$ may additionally represent hydrogen. Moreover, $R^{41}$ and $R^{42}$ may suitably together represent the residue of a dioxolane or optionally substituted benzene ring.

Suitably, $R^{42}$ represents hydrogen or methoxy, preferably hydrogen.

Suitably, $R^{43}$ and $R^{44}$ independently represent hydrogen, nitro, methyl, ethyl, vinyl or halogen, especially chlorine or iodine. Preferably, $R^{43}$ is hydrogen, ethyl or iodine. Preferably, $R^{44}$ is hydrogen.

Suitably, $R^{45}$ represents hydrogen, cyano, trifluoromethyl, nitro or halogen, preferably chlorine.

A particular sub-group of the compounds of formula IIB above is represented by the compounds of formula IIC and salts and prodrugs thereof:

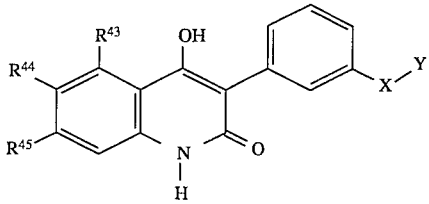 (IIC)

wherein

R$^{43}$, R$^{44}$ and R$^{45}$ are as defined above with reference to formula IIB;

X represents a moiety of formula —CH$_2$—, —CH=CH—, —C≡C—, —O—, —OCH$_2$—, —S—, —SO—, —NH—, —NHCH$_2$—, —NHCO— or —CO—; and Y represents a group of formula (i), (ii), (iii) or (iv):

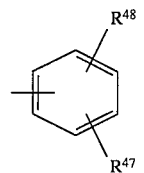 (i)

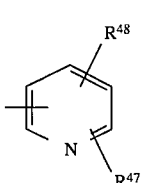 (ii)

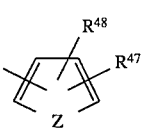 (iii)

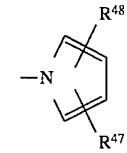 (iv)

in which Z represents oxygen, sulphur or NH; and

R$^{47}$ and R$^{48}$ independently represent hydrogen, C$_{1-6}$ alkyl, morpholinyl(C$_{1-6}$)alkyl, hydroxy, C$_{1-6}$ alkoxy, C$_{1-6}$ alkoxy(C$_{1-6}$)alkyl, C$_{1-6}$ alkoxy(C$_{1-6}$)alkoxy, C$_{1-6}$ alkylthio or di(C$_{1-6}$)alkylamino; or R$^{47}$ and R$^{48}$ together represent the residue of a benzene ring.

Particular values of R$^{47}$ and/or R$^{48}$ include hydrogen, methyl, morpholinylethyl, hydroxy, methoxy, methoxymethyl, methoxymethoxy, methylthio and dimethylamino. Suitably at least one of R$^{47}$ and R$^{48}$ is hydrogen.

Specific compounds within the scope of the present invention include:
7-chloro-4-hydroxy-3-(4-nitrophenyl)-2(1H)-quinolone;
7-chloro-4-hydroxy-3-(4-methoxyphenyl)-2(1H)-quinolone;
7-chloro-4-hydroxy-3-(2-nitrophenyl)-2(1H)-quinolone;
7-chloro-4-hydroxy-3-(4-trifluoromethylphenyl)-2(1H)-quinolone;
7-chloro-4-hydroxy-3-(3-methylphenyl)-2 (1H)-quinolone;
3-(4-benzyloxyphenyl)-7-chloro-4-hydroxy-2(1H)-quinolone;
7-chloro-3-(4-chlorophenyl)-4-hydroxy-2(1H)-quinolone;
7-chloro-3-(4-fluorophenyl)-4-hydroxy-2(1H)-quinolone;
7-chloro-4-hydroxy-3-(3-methoxyphenyl)-2(1H)-quinolone;
7-chloro-4-hydroxy-3-(3-iodophenyl)-2(1H)-quinolone;
3-(4-bromophenyl)-7-chloro-4-hydroxy-2(1H)-quinolone;
7-chloro-4-hydroxy-3-(3-nitrophenyl)-2(1H)-quinolone;
4-hydroxy-7-nitro-3-phenyl-2(1H)-quinolone;
7-chloro-3-(2,5-dimethoxyphenyl)-4-hydroxy-2(1H)-quinolone;
3-(2-bromophenyl)-7-chloro-4-hydroxy-2(1H)-quinolone;
3-(3-bromophenyl)-7-chloro-4-hydroxy-2(1H)-quinolone;
7-chloro-3-(2-fluorophenyl)-4-hydroxy-2(1H)-quinolone;
7-chloro-3-(3-fluorophenyl)-4-hydroxy-2(1H)-quinolone;
3-(4'-biphenyl)-7-chloro-4-hydroxy-2(1H)-quinolone;
7-chloro-3-(4-dimethylaminophenyl)-4-hydroxy-2(1H)-quinolone;
7-chloro-3-(2-chlorophenyl)-4-hydroxy-2(1H)-quinolone;
7-chloro-4-hydroxy-3-(2-methoxyphenyl)-2(1H)-quinolone;
7-chloro-4-hydroxy-3-(2-phenoxyphenyl)-2(1H)-quinolone;
7-chloro-4-hydroxy-3-(2-naphthyl)-2(1H)-quinolone;
7-chloro-4-hydroxy-3-(1-naphthyl)-2(1H)-quinolone;
3-(3-benzyloxyphenyl)-7-chloro-4-hydroxy-2(1H)-quinolone;
7-chloro-3-(3-chlorophenyl)-4-hydroxy-2(1H)-quinolone;
7-chloro-4-hydroxy-3-(3-phenoxyphenyl)-2(1H)-quinolone;
7-chloro-4-hydroxy-3-(4-phenoxyphenyl)-2(1H)-quinolone;
7-chloro-5-ethyl-4-hydroxy-3-phenyl-2(1H)-quinolone;
7-chloro-4-hydroxy-3-[3-(2-phenylethynyl)phenyl]-2(1H)-quinolone;
7-chloro-4-hydroxy-5-iodo-3-phenyl-2(1H)-quinolone;
7-chloro-4-hydroxy-3-(3,4-methylenedioxyphenyl)-2(1H)-quinolone;
7-chloro-4-hydroxy-3-phenyl-5-vinyl-2(1H)-quinolone;
7-chloro-4-hydroxy-3-(4-iodophenyl)-2(1H)-quinolone;
7-chloro-3-(3,5-dimethylphenyl)-4-hydroxy-2(1H)-quinolone;
7-chloro-5-ethyl-4-hydroxy-3-(3-phenoxyphenyl)-2(1H)-quinolone;
4-hydroxy-7-methyl-3-(3-phenoxyphenyl)-2(1H)-quinolone;
7-chloro-4-hydroxy-3-(3-phenylcarbonylphenyl)-2(1H)-quinolone;
7-chloro-4-hydroxy-3-[3-(3-thienylcarbonyl)phenyl]-2(1H)-quinolone;
7-chloro-3-[3-(3-furylcarbonyl)phenyl]-4-hydroxy-2(1H)-quinolone;
7-chloro-4-hydroxy-3-[3-(1-pyrrolylmethyl)phenyl]-2(1H)-quinolone;
7-chloro-4-hydroxy-3-[3-(1-indolylmethyl)phenyl]-2(1H)-quinolone;
7-chloro-4-hydroxy-3-[3-(3-thienylmethyl)phenyl]-2(1H)-quinolone;
7-chloro-4-hydroxy-3-[3-(4-methoxymethylbenzyl)phenyl]-2(1H)-quinolone;
3-(3-benzylphenyl)-7-chloro-4-hydroxy-2(1H)-quinolone;
7-chloro-4-hydroxy-3-[3-(4-methylthiobenzyl)phenyl]-2(1H)-quinolone;
7-chloro-4-hydroxy-3-[3-(4-methoxymethoxybenzyl)phenyl]-2(1H)-quinolone;
7-chloro-4-hydroxy-3-[3-(4-hydroxybenzyl)phenyl]-2(1H)-quinolone;
7-chloro-4-hydroxy-3-[4-(2-morpholin-1-ylethyl)benzyl]phenyl]-2(1H)-quinolone;
7-chloro-4-hydroxy-3-[4-(2-phenyl-cis-ethenyl)phenyl]-2(1H)-quinolone;

7-chloro-4-hydroxy-3-[3-(2-phenyl-trans-ethenyl)phenyl]-2(1H)-quinolone;

7-chloro-4-hydroxy-3-[3-(2-phenyl-cis-ethenyl)phenyl]-2(1H)-quinolone;

7-chloro-4-hydroxy-3-[3-(3-indolylmethyl)phenyl]-2(1H)-quinolone;

7-bromo-4-hydroxy-3-phenyl-2(1H)-quinolone;

7-chloro-4-hydroxy-3-[3-(2-pyridyloxy)phenyl]-2(1H)-quinolone;

7-chloro-4-hydroxy-3-[3-(3-thienyloxy)phenyl]-2(1H)-quinolone;

7-chloro-3-[3-(3-furyloxy)phenyl]-4-hydroxy-2(1H)-quinolone;

7-chloro-4-hydroxy-3-(3-phenylaminophenyl)-2(1H)-quinolone;

7-chloro-3-[3-(2-dimethylaminophenoxy)phenyl]-4-hydroxy-2(1H)-quinolone;

7-chloro-4-hydroxy-3-[3-(4-methoxybenzyl)phenyl]-2(1H)-quinolone;

7-chloro-4-hydroxy-3-[3-(3-methoxyphenoxy)phenyl]-2(1H)-quinolone;

7-chloro-4-hydroxy-3-[3-(2-methoxyphenoxy)phenyl]-2(1H)-quinolone;

7-chloro-4-hydroxy-3-[3-(2-methylphenoxy)phenyl]-2(1H)-quinolone;

3-(3'-biphenyl)-7-chloro-4-hydroxy-2(1H)-quinolone;

7-chloro-4-hydroxy-3-(3-phenylthiophenyl)-2(1H)-quinolone;

7-chloro-4-hydroxy-3-(3-phenylsulphonylphenyl)-2(1H)-quinolone;

7-chloro-4-hydroxy-3-(3-phenylcarbonylaminophenyl)-2(1H)-quinolone;

3-(3-benzylaminophenyl)-7-chloro-4-hydroxy-2(1H)-quinolone;

7-chloro-4-hydroxy-3-[3-(2-propenyloxy)phenyl]-2(1H)-quinolone;

7-chloro-4-hydroxy-3-[3-(2-methyl-2-propenyloxy)phenyl]-2(1H)-quinolone;

7-chloro-3-(2,5-dimethoxyphenyl)-4-hydroxy-2(1H)-quinolone;

7-chloro-3-(4-ethoxyphenyl)-4-hydroxy-2(1H)-quinolone;

7-chloro-4-hydroxy-3-[3-(4-methoxyphenoxy)phenyl]-2(1H)-quinolone;

7-chloro-4-hydroxy-3-[3-(4-methylphenoxy)phenyl]-2(1H)-quinolone;

and salts and prodrugs thereof.

The pharmaceutical compositions of this invention are preferably in unit dosage forms such as tablets, pills, capsules, powders, granules, sterile solutions or suspensions, or suppositories, for oral, intravenous, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurodegeneration, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day. In a particular embodiment, the compounds may be conveniently administered by intravenous infusion.

The compounds of formula I above, including the novel compounds according to the invention, may be prepared by a process which comprises cyclising a compound of formula III:

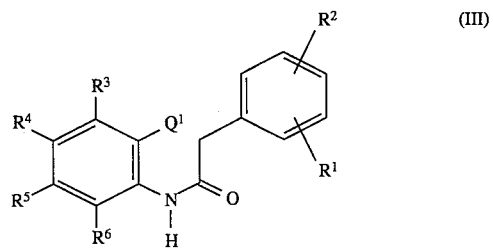

(III)

wherein $R^1$, $R^2$, $R^3$, $R^4$, $R^5$ and $R^6$ are as defined above; and $Q^1$ represents a reactive carboxylate moiety.

The reaction is conveniently carried out in the presence of a base, followed by a mild acidic work-up, as described, for example, in *J. Heterocycl. Chem.*, 1975, 12, 351. Suitable bases of use in the reaction include sodium hydride and potassium hexamethyldisilazide.

Suitable values for the reactive carboxylate moiety $Q^1$ include esters, for example $C_{1-4}$ alkyl esters; acid anhydrides, for example mixed anhydrides with $C_{1-4}$ alkanoic acids; acid halides, for example acid chlorides; orthoesters; and primary, secondary and tertiary amides.

Preferably, the group $Q^1$ represents methoxycarbonyl or ethoxycarbonyl.

The intermediates of formula III above may conveniently be prepared by reacting a compound of formula IV with a compound of formula V:

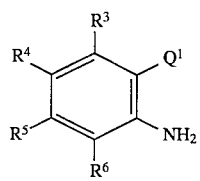

(IV)

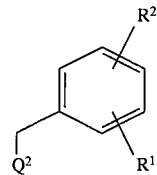

(V)

wherein $R^1$, $R^2$, $R^3$, $R^4$, $R^5$, $R^6$ and $Q^1$ are as defined above; and $Q^2$ represents a reactive carboxylate moiety.

The reaction is conveniently effected by mixing the reagents in an inert solvent, such as dichloromethane or 1,2-dichloroethane, and heating the reaction mixture at an elevated temperature, for example the reflux temperature of the solvent employed.

Suitable values for the reactive carboxylate moiety $Q^2$ correspond to those defined above for Preferably, the group $Q^2$ is an acid halide group, in particular an acid chloride group. A compound of formula V wherein $Q^2$ represents an acid chloride group may conveniently be prepared from the corresponding compound of formula V wherein $Q^2$ represents a carboxy group —$CO_2H$ by treatment with oxalyl chloride or thionyl chloride under standard conditions well known from the art.

In an alternative process, the compounds of formula I above, including the novel compounds according to the invention, may be prepared by cyclisation of a compound of formula VI:

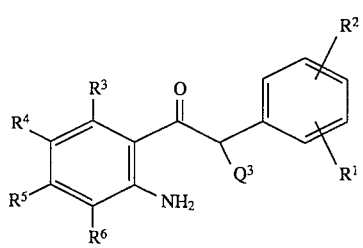

(VI)

wherein $R^1$, $R^2$, $R^3$, $R^4$, $R^5$ and $R^6$ are as defined above; and $Q^3$ represents a reactive carboxylate moiety.

The reaction is conveniently effected in the presence of a base such as potassium hexamethyldisilazide.

Suitable values for the reactive carboxylate moiety $Q^3$ correspond to those defined above for $Q^1$. Preferably, the group $Q^3$ represents a $C_{1-4}$ alkyl ester group such as methoxycarbonyl or ethoxycarbonyl.

Where $Q^3$ represents a $C_{1-4}$ alkyl ester group, the intermediates of formula VI may conveniently be prepared by Claisen ester condensation of a compound of formula IV with a compound of formula V, wherein $Q^1$ and $Q^2$ both represent $C_{1-4}$ alkyl ester groups. This involves heating the reactants together in the presence of a strong base such as potassium hexamethyldisilazide. Under appropriate conditions, the reactants may be converted in situ directly into the desired cyclised product of formula I without the necessity for isolation of the intermediate of formula VI.

In a further process, the compounds of formula I above, including the novel compounds according to the invention, may be prepared by cyclisation of a compound of formula VII:

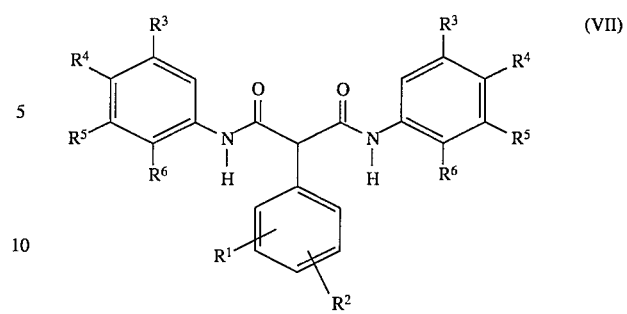

(VII)

wherein $R^1$, $R^2$, $R^3$, $R^4$, $R^5$ and $R^6$ are as defined above.

The cyclisation is conveniently effected by heating or by treatment of the compound of formula VII with phosphorus pentoxide in methanesulphonic acid, as described, for example, in *J. Heterocycl. Chem.*, 1988, 25, 857.

The intermediates of formula VII above may suitably be prepared by reacting a compound of formula VIII with a malonate derivative of formula IX:

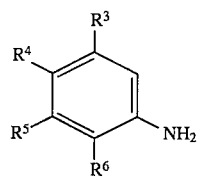

(VIII)

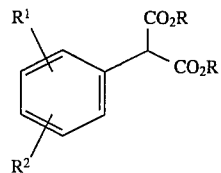

(IX)

wherein $R^1$, $R^2$, $R^3$, $R^4$, $R^5$ and $R^6$ are as defined above; and R represents $C_{1-4}$ alkyl.

The reaction is conveniently effected by heating a mixture of the reagents together for 15 to 20 hours, as described, for example, in *J. Heterocycl. Chem.*, 1988, 25, 857.

The aromatic intermediates of formulae IV, V, VIII and IX above, including the precursors of formula V wherein $Q^2$ represents —$CO_2H$, where they are not commercially available, may be prepared by the methods described in the accompanying Examples, or by methods analogous thereto which will be readily apparent to those skilled in the art.

It will be appreciated that any compound of formula I, IA or IB initially obtained from any of the above processes may, where appropriate, subsequently be elaborated into a further desired compound of formula I, IA or IB respectively using techniques known from the art.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene, *Protective Groups in Organic Synthesis*, John Wiley & Sons, 1981. The protecting groups may be removed at a convenient subsequent stage using methods known from the art.

The following Examples illustrate the preparation of compounds according to the invention.

The compounds useful in this invention potently and selectively block responses to NMDA and/or AMPA in a brain slice from rat cortex, and inhibit the binding of agonists and antagonists to the strychnine-insensitive site present on the NMDA receptor and/or AMPA binding to rat forebrain membranes.

Cortical Slice Studies

The effects of compounds of the invention on responses to NMDA and AMPA were assessed using the rat cortical slice as described by Wong et al., *Proc. Natl. Acad. Sci. USA*, 1986, 83, 7104. The apparent equilibrium constant ($K_b$) was calculated from the righthand shift in the NMDA or AMPA concentration-response curves produced by the compound under test. Of those compounds of the accompanying Examples which were tested, all were found to possess a $K_b$ value in response to NMDA of below 150 μM. The compound of Example 12 was tested and was found to possess a $K_b$ value in response to AMPA of below 150 μM.

Binding Studies

The ability of test compounds to displace $^3$H-L- 689,560 (trans-2-carboxy-5,7-dichloro-4-phenylaminocarbonylamino- 1,2,3,4-tetrahydroquinoline) binding to the strychnine-insensitive site present on the NMDA receptor of rat forebrain membranes was determined by the method of Grimwood et al., *Proceedings of The British Pharmacological Society*, July 1991, Abstract C78. The concentration of the compounds of the accompanying Examples required to displace 50% of the specific binding ($IC_{50}$) is below 50 μM in each case. NMR spectra were obtained at 360 MHz unless otherwise stated. Melting points are uncorrected.

EXAMPLE 1

7-Chloro-4-hydroxy-3-(3-methoxyphenyl)-2(1H)-quinolone

3-Methoxyphenylacetyl chloride (1.11 g, 6 mmol) was added to methyl 2-amino-4-chlorobenzoate (0.93 g, 5 mmol) in dichloromethane (30 ml) and the solution stirred under reflux for 18 h. The oily residue remaining on evaporation of the solvent was triturated with diethyl ether to afford methyl 4-chloro-2-(3-methoxyphenyl)acetamidobenzoate as a colourless solid (1.51 g), m.p. 144°–146° C.

To a solution of the foregoing amide (0.50 g, 1.5 mmol) in tetrahydrofuran (20 ml) was added a solution of potassium hexamethyldisilazide in toluene (0.5M, 8 ml, 4 mmol) and the resulting mixture stirred for 1.5 h under a nitrogen atmosphere. Methanol (3 ml) was then added and the solution evaporated. The residue remaining was partitioned between diethyl ether (10 ml) and aqueous sodium hydroxide (0.5M, 20 ml) and the aqueous layer acidified with hydrochloric acid (5M). The precipitated solid was collected, washed with water and recrystallised from dimethylformamide to afford the title compound as a colourless solid; m.p.>320° C. (dec) (Found: C, 63.44; H, 3.89; N, 4.54. $C_{16}H_{12}ClNO_3$ requires C, 63.69; H, 4.01; N, 4.64%); $\delta_H$ (DMSO-d$_6$) 3.76 (3H, s, OCH$_3$), 6.88–6.94 (3H, m, ArH), 7.20 (1H, dd, J 8.7 and 2.1 Hz, 6-H), 7.28–7.32 (2H, m, ArH), 7.91 (1H, d, J 8.7 Hz, 5-H), 10.24 (1H, br s, OH) and 11.48 (1H, s, NH); m/z 301 (M$^+$).

Unless stated otherwise, the following examples were prepared in an analogous manner from the appropriate arylacetyl chloride. The acid chlorides could be prepared from the acids by treatment with excess oxalyl chloride and catalytic DMF in dichloromethane at room temperature for 1 h, followed by evaporation.

EXAMPLE 2

7-Chloro-4-hydroxy-3-(3-iodophenyl)-2(1H)-quinolone

M.p.>350° C. (from DMF) (Found: C, 45.56; H, 1.99; N, 3.39. $C_{15}H_9ClINO_2$ requires C, 45.31; H, 2.28; N, 3.52%); $\delta_H$ (DMSO-d$_6$) 7.19–7.24 (2H, m, ArH and 6-H), 7.32 (1H, d, J 1.9 Hz, 8-H), 7.39 (1H, d, J 7.8 Hz, ArH), 7.69–7.71 (2H, m, 2' and ArH), 7.94 (1H, d, J 9.4 Hz, 5-H), 10.50 (1H, br s, OH), and 11.57 (1H, s, NH); m/z 397 (M$^+$).

EXAMPLE 3

7-Chloro-4-hydroxy-3-(4-iodophenyl)-2(1H)-quinolone

M.p.>350° C. (from DMF/water) (Found: C, 45.51; H, 2.10; N, 3.45. $C_{15}H_9ClINO_2$ requires C, 45.31; H, 2.28; N, 3.52%); $\delta_H$ (DMSO-d$_6$) 7.18–7.23 (3H, m, ArH), 7.31 (1H, d, J 1.9 Hz, 8-H), 7.75 (2H, d, J 8.3 Hz, Ar'H), 7.93 (1H, d, J 8.7 Hz, 5-H), 10.42 (1H, br s, OH), and 11.53 (1H, s, NH); m/z 397 (M$^+$).

EXAMPLE 4

7-Chloro-4-hydroxy-3-(2-phenoxyphenyl)-2(1H)-quinolone

M.p. 284°–288° C. (from DMF/Water) (Found: C, 68.77; H, 4.04; N, 3.94. $C_{21}H_{14}ClNO_3.0.125H_2O$ requires C, 68.91; H, 3.92; N, 3.88%); $\delta_H$ (DMSO-d$_6$) 6.87 (1H, d, J 7.7 Hz, ArH), 6.96–7.03 (3H, m, ArH), 7.16–7.20 (2H, m, ArH), 7.26–7.37 (5H, m, ArH), 7.87 (1H, d, J 8.7 Hz, 5-H), 10.29 (1H, br s, OH), and 11.41 (1H, s, NH); m/z 363 (M$^+$).

EXAMPLE 5

7-Chloro-4-hydroxy-3-(3-phenoxyphenyl)-2(1H)-quinolone

M.p. 303°–306° C. (from DMF/water); (Found: C, 69.09; H, 3.96; N, 3.82. $C_{21}H_{14}ClNO_3$ requires C, 69.33; H, 3.88; N, 3.85%); $\delta_H$ (DMSO-d$_6$) 6.96 (1H, dd, J 7.4, 1.8 Hz, 4'-H), 7.01 (1H, s, 2'-H), 7.08–7.14 (4H, m, ArH), 7.20 (1H, dd, J 8.8, 2.0 Hz, 6-H), 7.31 (1H, d, J 2.0 Hz, 8-H), 7.36–7.43 (3H, m, ArH), 7.92 (1H, d, J 8.8 Hz, 5-H), 10.40 (1H, br s, OH), and 11.53 (1H, s, NH); m/z 363 (M$^+$).

EXAMPLE 6

7-Chloro-4-hydroxy-3-(4-phenoxyphenyl)-2(1H)-quinolone

M.p. 274°–276° C. (from DMF/water) (Found: C, 68.83; H, 3.93; N, 3.75. $C_{21}H_{14}ClNO_3.0.125H_2O$ requires C, 68.91; H, 3.92; N, 3.83%); $\delta_H$ (DMSO-d$_6$) 7.01–7.08 (4H, m, ArH), 7.15 (1H, t, J 7.5 Hz, 4"-H), 7.21 (1H, dd, J 8.7 and 2.1 Hz, 6-H), 7.32 (1H, d, J 2.1H, 8-H), 7.37–7.44 (4H, m, ArH), 7.93 (1H, d, J 8.7 Hz, 5-H), 10.29 (1H, br s, OH), and 11.55 (1H, s, NH); m/z 363 (M+).

EXAMPLE 7

7-Chloro-4-hydroxy-3-(3-phenylethynylphenyl)-2(1H)-quinolone

To a solution of methyl 2-(3-iodophenylacetamido)-4-chlorobenzoate (m.p. 100°–101° C.; prepared by the general procedure described above; 860 mg, 2 mmol) in triethylamine (20 ml) and tetrahydrofuran (5 ml), was added copper (I) iodide (5 mg), bis(triphenylphosphine)palladium (II) dichloride (20 mg) and phenylacetylene (0.33 ml, 306 mg, 3 mmol), and the mixture stirred overnight at room temperature and then for 5 h at reflux. The solvents were removed, the residue partitioned between ethyl acetate (30 ml) and aqueous citric acid (10%, 25 ml), and the organic layer washed with water (25 ml) and brine (25 ml). After drying (MgSO$_4$), the solution was evaporated and the residue subjected to chromatography on silica gel (4:1 petrol-ethyl acetate as eluant) to afford methyl 4-chloro-2-(3-phenylethynylphenyl)acetamidobenzoate as a colourless gum (824mg); $\delta_H$ (CDCl$_3$) 3.75 (2H, s, —CH$_2$—), 3.87 (3H, s, CO$_2$Me), 7.03 (1H, dd, J 9.4 and 2.1 Hz, 5-H), 7.33–7.38 (5H, m, ArH), 7.48–7.55 (4H, m, ArH), 7.91 (1H, d, J 9.4 Hz, 6-H), 8.82 (1H, d, J 2.1 Hz, 3-H), and 11.14 (1H, br s, —NHCO—).

A portion of this amide was cyclised as before to afford the title compound m.p. 297°–300° C. (from DMF/water); (Found: C, 74.18; H, 3.62; N, 3.69. C$_{23}$H$_{14}$ClNO$_2$ requires C, 74.30; H, 3.80; N, 3.77%); $\delta_H$ (DMSO-d$_6$) 7.23 (1H, dd, J 8.6 and 2.0 Hz, 6-H), 7.33 (1H, d, J 2.0 Hz, 8-H), 7.41–7.51 (9H, m, ArH), 7.95 (1H, d, J 8.6 Hz, 5-H), 10.50 (1H, br s, OH), and 11.58 (1H, s, NH); m/Z 371 (M+).

EXAMPLE 8

7-Chloro-4-hydroxy-3-(2-nitrophenyl)-2(1H)-quinolone

M.p. 298°–300° C. (from DMF/water) (Found: C, 56.74; H, 2.86; N, 8.85; C$_{15}$H$_9$ClN$_2$O$_4$ requires C, 56.89; H, 2.86; N, 8.85%); $\delta_H$ (DMSO-d$_6$) 7.26 (1H, dd, J 8.6 and 2.1 Hz, 6-H), 7.33(1H, d, J=2.1 Hz, 8-H), 7.52 (1H, d, J 6.4 Hz, 6'-H), 7.60 (1H, t, J 7.6 Hz, 5'-H), 7.75 (1H, t, J 7.6 Hz, 4' 7.96 (1H, d, J 8.7 Hz, 5-H), 8.06 (1H, d, J 7.1 Hz, 3'-H), and 11.63 (1H, s, NH); m/z 316 (M+).

EXAMPLE 9

7-Chloro-4-hydroxy-3-(4-methoxyphenyl)-2(1H)-quinolone

M.p.>350° C. (from DMF/water); $\delta_H$ (250 MHz; DMSO-d$_6$) 3.81 (3H, s, OCH$_3$); 6.96 (2H, d, J 7.2 Hz, 2'-H, 6'-H), 7.21 (1H, dd, J 8.6 and 2.1 Hz, 6-H), 7.29 (2H, d, J 7.2 Hz, 3'-H, 5'-H), 7.33 (1H, d, J=2.1 Hz, 8-H), 7.96 (1H, d, J 8.7 Hz, 5-H), and 11.49 (1H, s, NH); m/z 301 (M+) (Found: m/z 301.0478; C$_{16}$H$_{12}$ClNO$_3$ requires m/z 301.0507).

EXAMPLE 10

3-(4-Bromophenyl)-7-chloro-4-hydroxy-2(1H)-quinolone

M.p.>350° C. (from DMF/water) (Found: C, 51.10; H, 2.55; N, 3.92; C$_{15}$H$_9$BrClNO$_2$ requires C, 51.38; H, 2.58; N, 3.99%); $\delta_H$ (250 MHz; DMSO-d$_6$) 7.23 (1H, dd, J 8.6 and 2 Hz, 6-H), 7.32–7.40 (3H, m, 2'-H, 6'-H, 8-H), 7.58 (2H, d, J 10.8 Hz, 3'-H, 5'-H), 7.90 (1H, d, J 8.6 Hz, 5-H), and 11.48 (1H, s, NH); m/z 351 (M+).

EXAMPLE 11

7-Chloro-4hydroxy-3-(3-nitrophenyl)-2(1H)-quinolone m.p. 329°–332° C. (from DMF/water) (Found: C, 56.63; H, 2.58; N, 8.66; C$_{15}$H$_9$ClN$_2$O$_4$ requires C, 56.89; H, 2.86; N, 8.85%); $\delta_H$ (DMSO-d$_6$) 7.26 (1H, dd, J 8.6 and 2 Hz, 6-H), 7.35 (1H, s, 8-H), 7.69 (1H, t, J 8 Hz, 5'-H), 7.88 (1H, d, J 7.7 Hz, 5-H), 7.99 (1H, d, J 8.7 Hz, 6'-H), 8.17 (1H, d, J 9.6 Hz, 4'-H), 8.26 (1H, s, 2'-H), and 11.67 (1H, s, NH); m/z 316 (M+).

EXAMPLE 12

4-Hydroxy-7-nitro-3-phenyl-2(1H)-quinolone

M.p.>330° C. (from DMF/water) (Found: C, 62.98; H, 3.47; N, 9.82; C$_{15}$H$_{10}$N$_2$O$_4$, 0.2H$_2$O requires C, 63.02; H, 3.67; N, 9.80%); $\delta_H$ (DMSO-d$_6$6) 7.32–7.45 (5H, m, ArH), 7.97 (1H, dd, J 8.8 and 2.3 Hz, 6-H), 8.13–8.16 (2H, m, 5-H, 8-H), 10.57 (1H, br s, OH), and 11.88 (1H, s, NH); m/z 282 (M+).

EXAMPLE 13

7-Chloro-4-hydroxy-3-(2,5-dimethoxyphenyl)-2(1H)-quinolone

M.p. 280°–282° C. (from DMF/water) (Found: C, 61.35; H, 4.14; N, 4.29; C$_{17}$H$_{14}$ClNO$_4$, 0.1 H$_2$O requires C, 61.21; H, 4.29; N, 4.29%); $\delta_H$ (DMSO-d$_6$) 3.71 (3H, s, OCH$_3$), 3.71 (3H, s, OCH$_3$), 6.70 (1H, d, J 3 Hz, 6'-H), 6.88 (2H, m, 3', 4'-H), 7.19 (1H, dd, J 8.6 and 2.1 Hz, 6-H), 7.30 (1H, s, 8-H), 7.86 (1H, d, J 8.6 Hz, 5-H), 9.95 (1H, br s, OH), and 11.42 (1H, s, NH); m/z 331 (M+).

EXAMPLE 14

3-(3-Benzyloxyphenyl)-7-chloro-4-hydroxy-2(1H)-quinolone

M.p. 293°–295° C. (from DMF/water) (Found: C, 69.23; H, 4.39; N, 3.73; C$_{22}$H$_{16}$ClNO$_3$.0.25H$_2$O requires C, 69.11; H, 4.35; N, 3.66%); $\delta_H$ (DMSO-d$_6$) 5.10 (2H, s, CH$_2$ Ph), 6.93–7.08 (3H, m, ArH), 7.21 (1H, dd, J 8.6 and 2.0 Hz, 6-H), 7.19–7.47 (7H, m, ArH), 7.92 (1H, d, J 8.6 Hz, 5-H), 10.26 (1H, br s, OH), and 11.52 (1H, s, NH); m/z 377 (M+).

EXAMPLE 15

7-Chloro-4-hydroxy-3-(1-naphthyl)-2(1H)-quinolone

M.p.>350° C. (from DMF/water) (Found: C, 70.83; H, 4.05; N, 4.34; C$_{19}$H$_{12}$ClNO$_2$ requires C, 70.92; H, 3.76; N, 4.35%); $\delta_H$ (DMSO-d$_6$) 7.23 (1H, dd, J 8.6 and 2.0 Hz, 6-H), 7.36–7.58 (6H, m, ArH), 7.92–7.97 (3H, m, ArH), 10.17 (1H, br s, OH), and 11.58 (1H, s, NH); m/z 321 (M+).

EXAMPLE 16

7-Chloro-4-hydroxy-3-(2-naphthyl)-2(1H)-quinolone

M.p.>350° C. (from DMF/water) (Found: C, 70.62; H, 4.14; N, 4.37; C$_{19}$H$_{12}$ClNO$_2$ requires C, 70.92; H, 3.76; N, 4.35%); $\delta_H$ (DMSO-d$_6$) 7.23 (1H, dd, J 8.6 and 2.0 Hz, 6-H), 7.34 (1H, d, J 1.7 Hz, 8-H), 7.48–7.52 (3H, m, ArH), 7.90–7.96 (5H, m, ArH), and 11.58 (1H, s, NH); m/z 321 (M+).

EXAMPLE 17

7-Chloro-4-hydroxy-3-(3,4-methylenedioxyphenyl)-2(1H) quinolone

M.p.>350° C. (from DMF/water) (Found: C, 60.61; H, 3.00, N, 4.47; $C_{16}H_{10}ClNO_4$ requires C, 60.87; H, 3.19; N, 4.34%); $\delta_H$ (DMSO-$d_6$) 6.02 (2H, s,—OCH$_2$O—), 6.81 (1H, dd, J 8.0 and 1.7 Hz, 6'-H), 6.87 (1H, d, J 1.7 Hz, 2'-H), 6.93 (1H, d, J 8.0 Hz, 5'-H), 7.19 (1H, dd, J 8.6 and 2.0 Hz, 6-H), 7.30 (1H, d, J 2.0 Hz, 8-H), 7.90 (1H, d, J 8.6 Hz, 5-H), 10.16 (1H, br s, OH), and 11.49 (1H, s, NH); m/z 315 (M$^+$).

EXAMPLE 18

3-(4-Benzyloxyphenyl)-7-chloro-4-hydroxy-2(1H) quinolone

M.p.>350° C. (from DMF) (Found: C, 69.69; H, 4.03; N, 3.60; $C_{22}H_{16}ClNO_3$ requires C, 69.94; H, 4.27; N, 3.71%); $\delta_H$ (DMSO-$d_6$) 5.15 (2H, s, C$\underline{H}_2$Ph), 7.03 (2H, m, ArH), 7.20 (1H, dd, J 8.6 and 2.0 Hz, 6-H), 7.28–7.49 (8H, m, ArH), 7.91 (1H, d, J 8.6 Hz, 5-H), 10.13 (1H, br s, OH), and 11.49 (1H, s, NH); m/z 377 (M$^+$).

EXAMPLE 19

7-Chloro-4-hydroxy-3-(3-methylphenyl)-2(1H) quinolone

M.p.>350° C. (from DMF/water) (Found: C, 67.15; H, 4.11; N, 4.82; $C_{16}H_{12}ClNO_2$ requires C, 67.26; H, 4.23; N, 4.90%); $\delta_H$ (DMSO-$d_6$) 2.35 (3H, s, PhC$\underline{H}_3$), 7.11–7.17 (4H, m, ArH), 7.26–7.31 (2H, m, ArH), 7.91 (1H, d, J 8.6 Hz, 5-H), and 11.49 (1H, s, NH); m/z 285 (M$^+$).

EXAMPLE 20

7-Chloro-4-hydroxy-3-(4-trifluoromethylphenyl)-2(1H) quinolone

M.p. 325°–327° C. (dec) (from DMF/water) (Found: C, 56.43; H, 2.58; N, 4.03; $C_{16}H_9ClF_3NO_2$ requires C, 56.57; H, 2.67; N, 4.12%); $\delta_H$ (DMSO-$d_6$) 7.23 (1H, dd, J 8.6 and 2.0 Hz, 6-H), 7.34 (1H, d, J 2.0 Hz, 8-H), 7.61 (2H, d, J 8.0 Hz, 2'-H, 6'-H), 7.74 (2H, d, J 8.0 Hz, 3'-H, 5'-H), 7.98 (1H, d, J 8.6 Hz, 5-H), and 11.64 (1H, s, NH); m/z 339 (M$^+$).

EXAMPLE 21

7-Chloro-4-hydroxy-3(4-nitrophenyl)-2(1H) quinolone

M.p.>350° C. (from DMF/water) (Found: C, 56.08; H, 2.76; N, 8.63; $C_{15}H_9ClN_2O_4 \cdot 0.25H_2O$ requires C, 56.09; H, 2.98; N, 8.72%); $\delta_H$ (DMSO-$d_6$) 7.24 (1H, dd, J 8.6 and 2.0 Hz, 6-H), 7.34 (1H, d, J 1.8 Hz, 8-H), 7.72 (2H, d, J 8.8 Hz, 2'-H, 6'-H), 8.00 (1H, d, J 8.6 Hz, 5-H), 8.24 (2H, d, J 8.8 Hz, 3'-H, 5'-H), and 11.65 (1H, s, NH); m/z 316 (M$^+$).

EXAMPLE 22

7-Chloro-3-(4-chlorophenyl)-4-hydroxy-2(1H)-quinolone

M.p.>300° C. (from DMF/water) (Found: C, 58.62; H, 2.94; N, 4.33; $C_{15}H_9Cl_2NO_2$ requires C, 58.85; H, 2.96; N, 4.58%); $\delta_H$ (DMSO-$d_6$) 7.22 (1H, dd, J 8.6, 2.0 Hz, 6-H), 7.31 (1H, s, 8-H), 7.32–7.46 (4H, m, 2'-H, 3'-H, 5'-H, 6'-H), 7.93–7.95 (1H, d, J 8.6 Hz, 5-H), 10.43 (1H, br s, OH), and 11.57 (1H, s, NH); m/z 305 (M$^+$).

EXAMPLE 23

7-Chloro-3-(4-fluorophenyl)-4-hydroxy-2(1H)-quinolone

M.p. 335°–337° C. (from DMF/water) (Found: C, 62.09; H, 3.03; F, 6.25; N, 4.67. $C_{15}H_9ClFNO_2$ requires C, 62.19; H, 3.13; F, 6.56; N, 4.84%); $\delta_H$ (DMSO-$d_6$), 7.13–7.18 (3H, m, 6-H, 3'-H, 5'-H), 7.32 (1H, s, 8-H), 7.38–7.42 (2H, m, 3'-H, 5'-H), 7.92–7.94 (1H, d, J 8.6 Hz, 5-H), 10.19 (1H, br s, OH), and 11.54 (1H, s, NH); m/z 289 (M$^+$).

EXAMPLE 24

3-(4-Biphenyl)-7-chloro-4-hydroxy-2(1H)-quinolone

M.p.>300° C. (from DMF) (Found: C, 72.15; H, 4.01; N, 4.11. $C_{21}H_{14}ClNO_2$ requires C, 72.50; H, 4.05; N, 4.03%); $\delta_H$ (DMSO-$d_6$) 7.20–7.24 (1H, dd, J 8.6 Hz, 6-H), 7.32 (1H, s, 8-H), 7.32–7.40 (1H, m, Ar-H), 7.49–7.51 (4H, m, Ar-H), 7.68–7.72 (4H, m, Ar-H), 7.94–7.98 (1H, d, J 8.6 Hz, 5-H). 10.37 (1H, br s, OH), and 11.56 (1H, s, NH); m/z 347 (M$^+$).

EXAMPLE 25

7-Chloro-4-hydroxy-3-(2-methoxyphenyl)-2(1H)-quinolone

M.p.>300° C. (from DMF) (Found: C, 63.26; H, 4.15; N, 4.52; $C_{16}H_{12}ClNO_3$ requires C, 63.69; H, 4.01; N, 4.64%); $\delta_H$ (DMSO-$d_6$), 3.69 (3H, s, OCH$_3$), 6.94–6.99 (1H, m, Ar-H), 7.03 (1H, d, J 8.1 Hz, Ar-H), 7.10 (1H, dd, J 7.4, 1.7 Hz, Ar-H), 7.18 (1H, dd, J 8.6, 2.0 Hz, 6-H), 7.30–7.36 (2H, m, Ar-H, 8-H), 7.86 (1H, d, J 8.6 Hz, 5-H), 9.92 (1H, br s, OH), and 11.42 (1H, s, NH); m/z 301 (M$^+$).

EXAMPLE 26

7-Chloro-3-(4-dimethylaminophenyl)-4-hydroxy-2(1H)-quinolone

M.p.>300° C. (from DMF) (Found: C, 64.42; H, 5.02; N, 8.79. $C_{17}H_{15}ClN_2O_2$ requires C, 64.87; H, 4.80; N, 8.90%); $\delta_H$ (DMSO-$d_6$) 2.93 (6H, s, 2×CH$_3$), 6.76 (2H, d, J 8.7, 2'-H, 6'-H), 7.17–7.29 (4H, m, 3'-H, 5'-H, 6-H, 8-H), 7.89 (1H, d, J 8.6 Hz, 5-H), 8.94 (1H, br s, OH), and 11.44 (1H, s, N-H); m/z 314 (M$^+$).

EXAMPLE 27

7-Chloro-3-(2-chlorophenyl)-4-hydroxy-2(1H)-quinolone

M.p.>300° C. (from DMF) (Found: C, 58.36; H, 3.19; N, 4.54. $C_{15}H_9Cl_2NO_2$ requires C, 58.86; H, 2.96; N, 4.58%); $\delta_H$ (DMSO-$d_6$), 7.21–7.53 (6H, m, ArH), 7.93 (1H, d, J 8.6 Hz, 5-H), 10.48 (1H, br s, OH), and 11.56 (1H, s, NH); m/z 306 (M$^+$).

EXAMPLE 28

7-Chloro-3-(3-chlorophenyl)-4-hydroxy-2(1H)-quinolone

M.p.>300° C. (from DMF) (Found: C, 58.64; H, 3.06; N, 4.60. $C_{15}H_9Cl_2NO_2$ requires C, 58.84; H, 2.96; N, 4.57%); $\delta_H$ (DMSO-$d_6$) 7.22 (1H, dd, J 8.6, 2.0 Hz, 6-H), 7.32–7.45 (5H, m, 8-H, 3'-H, 4'-H, 5'-H, 6'-H), 7.94 (1H, d, J 8.6 Hz, 5-H), 10.54 (1H, br s, OH), and 11.60 (1H, s, NH); m/z 306 (M$^+$).

EXAMPLE 29

3-(2-Bromophenyl)-7-chloro-4-hydroxy-2(1H)-quinolone

M.p. 357°–358° C. (from DMF) (Found: C, 51.58; H, 2.47; N, 3.86%); $C_{15}H_9BrClNO_2$ requires C, 51.39; H, 2.59; N, 4.00; $\delta_H$ (DMSO-$d_6$) 7.41 (6H, m, ArH, 6-H, 8-H), 7.91 (1H, d, J 8.6 Hz, 5-H), and 11.54 (1H, s, NH); m/z 351 (M$^+$).

EXAMPLE 30

3-(3-Bromophenyl)-7-chloro-4-hydroxy-2(1H)-quinolone

M.p. 358° C. (from DMF) (Found: C, 49.38; H, 2.54; N, 3.76; $C_{15}H_9BrClNO_2.0.7H_2O$ requires C, 49.60; H, 2.89; N, 3.86%); $\delta_H$ (DMSO-$d_6$) 7.23 (1H, dd, J 8.5, 2.0 Hz, 6-H), 7.38 (3H, m, ArH), 7.51 (1H, m, ArH), 7.54 (1H, d, J 2.0 Hz, 8-H), 7.95 (1H, d, J 8.5 Hz, 5-H), and 11.60 (1H, s, NH); m/z 351 (M$^+$).

EXAMPLE 31

7-Chloro-3-(2-fluorophenyl)-4-hydroxy-2(1H)-quinolone

M.p.>350° C. (from DMF) (Found: C, 60.87; H, 3.10; N, 4.65; $C_{15}H_9ClFNO_2$ requires C, 60.68; H, 3.33; N, 4.72); $\delta_H$ (DMSO-$d_6$) 7.32 (6H, m, ArH, 6-H, 8-H), 7.94 (1H, d, J 8.6 Hz, 5-H), and 11.59 (1H, s, NH); m/z 290 (M$^+$).

EXAMPLE 32

7-Chloro-3-(3-fluorophenyl)-4-hydroxy-2(1H)-quinolone

M.p.>350° C. (from DMF) (Found: C, 61.66; H, 3.14; N, 4.77; $C_{15}H_9ClFNO_2$ requires C, 61.43; H, 3.23; N, 4.78); $\delta_H$ (DMSO-$d_6$) 7.22 (4H, m, ArH, 6-H), 7.33 (1H, d, J 2.2 Hz, 8-H), 7.44 (1H, m, ArH), 7.95 (1H, d, J 8.6 Hz, 5-H), and 11.60 (1H, s, NH); m/z 290 (M$^+$).

EXAMPLE 33

7-Chloro-3-(3,5-dimethylphenyl)-4-hydroxy-2(1H)-quinolone

M.p. 369° C. (from DMF) (Found: C, 67.91; H, 4.66; N, 4.61; $C_{17}H_{14}ClNO_2$ requires C, 68.12; H, 4.71; N, 4.67); $\delta_H$ (DMSO-$d_6$) 2.29 (6H, s, 2×CH$_3$), 6.94 (3H, m, ArH), 7.20 (1H, dd, J 8.6 and 1.9 Hz, 6-H), 7.35 (1H, d, J 1.9 Hz, 8-H), 7.90 (1H, d, J 8.6 Hz, 5-H), and 11.50 (1H, s, NH); m/z (M$^+$).

EXAMPLE 34

7-Chloro-4-hydroxy-5-iodo-3-phenyl-2(1H)-quinolone

A solution of 3-chloro-5-iodoaniline (63.41 g) in water (150 ml), concentrated hydrochloric acid (22.1 ml) and 1,4-dioxan (60 ml) was added to a mixture of chloral hydrate (90.24 g) and sodium sulphate (650 g) in water (600 ml) which had been warmed to 50° C. Hydroxylamine hydrochloride (110.56 g) in water (250 ml) was then added and the reaction heated at reflux for 45 min before being allowed to cool to room temperature and the resultant yellow precipitate of 3-chloro-5-iodophenylisonitrosacetanilide filtered off, washed with water and dried in vacuo over silica gel.

A sample of the isonitrosoacetanilide (45 g) was added portionwise to pre-warmed concentrated sulphuric acid (175 ml, 50° C.) keeping the internal temperature between 50° C. and 70° C., using an ice bath. After complete addition the reaction was heated at 80° C. for 10 minutes before being allowed to cool to room temperature and poured onto ten times the reaction volume of ice. The resultant slurry was swirled vigorously and left to stand for one hour before filtering off the resulting rust coloured precipitate, washing with water and drying in vacuo over phosphorus pentoxide. This yielded a mixture of 6-chloro-4-iodo and 4-chloro-6-iodo isatins. $\delta_H$ (DMSO-$d_6$) 6.98 (1H, d, J 1.6 Hz, H-5 or H-7), 7.25 (1H, d, J 1.0 Hz, H-5' or H-7'); 7.50 (1H, d, J 1.0 Hz, H-5' or H-7'), 7.55 (1H, d, J 1.6 Hz, H-5 or H-7), 11.18 (1H, s, NH), and 11.26 (1H, s, N'H).

30% hydrogen peroxide (35.7 ml) was added portionwise to a solution of the mixture of the above isatins (53.68 g) at room temperature in 1N sodium hydroxide solution (525 ml). Once effervescence had stopped the reaction was cautiously neutralised with 2N hydrochloric acid and filtered to remove lo insolubles before acidifying to pH 2–3. The resultant sandy yellow precipitate was filtered off and washed with water before drying in vacuo over phosphorus pentoxide to yield a mixture of the 2-amino-4-chloro-6-iodo and 2-amino-6-chloro-4-iodo benzoic acids (10.56 g). Dissolving the mixture of isomers (8 g) in boiling acetone and reducing the volume until a solid started to crystallise out, resulted in the formation of the Schiff's base (enriched (10:1)in the more prevalent 4-chloro-6-iodo isomer). Hydrolysis of this imine with 2N hydrochloric acid yielded the amino benzoic acid. Repetition of this process gave 2-amino-4-chloro- 6-iodobenzoic acid (3.75 g) in >95% purity. $\delta_H$ (DMSO-$d_6$) 6.79 (1H, d, J 1.9 Hz, H-3 or H-5), 7.05 (1H, d, J 1.9 Hz, H-3 or H-5).

Treatment of an ethereal solution of the acid (2.68 g) with diazomethane and concentration in vacuo yielded the desired methyl 2-amino-4-chloro-6-iodobenzoate (2.81 g). $\delta_H$ (DMSO-$d_6$) 3.61 (3H, s, CH$_3$), 5.89 (2H, s, NH$_2$), 6.78 (1H, d, J 1.9 Hz, H-3 or H-5), 7.04 (1H, d, J 1.9 Hz, H-3 or H-5); which was used as described above to prepare methyl 4-chloro-6-iodo-2-phenylacetamidobenzoate, cyclisation of which as described above gave the title compound; sublimes at 256° C. (from DMF/water); (Found: C, 45.77; H, 2.24; N, 3.41. $C_{15}H_9ClINO_2.0.08$ DMF requires C, 45.37; H, 2.39; N, 3.75%); $\delta_H$ (DMSO-$d_6$) 7.30–7.42 (6H, m, ArH and 6-H or 8-H), 7.82 (1H, d, J 2.0 Hz, 6-H or 8-H), 10.28 (1H, br s, OH), and 11.62 (1H, s, NH); m/z 397 (M$^+$).

EXAMPLE 35

7-Chloro-4-hydroxy-3-phenyl-5-vinyl-2(1H)-quinolone

Bis(triphenylphosphine)palladium (II) chloride (0.1 g) was added to a solution of methyl 2-amino-4-chloro-6-iodobenzoate (0.52 g), dry lithium chloride (0.25 g) and vinyltributyltin (0.6 ml) in dry DMF (10 ml) under N$_2$. The mixture was heated at 60° C. for 45 mins, allowed to cool to room temperature and diluted with ethyl acetate. The organics were washed with water and then brine before being dried over magnesium sulphate. The solvent was removed in vacuo to leave a brown oil which was purified by silica gel chromatography eluting with 10% ethyl acetate in hexane, yielding 0.26 g of the desired methyl 2-amino- 4-chloro-6-vinyl benzoate. $\delta_H$ (250 MHz; DMSO-$d_6$) 3.80 (3H, s, CH$_3$), 5.26 (1H, d, J 11.0 Hz, C$\underline{H}_A$H$_B$, H$_A$<u>trans</u> to Ar), 5.62 (1H, d, J 17.5 Hz, CH$_A$$\underline{H}_B$, H$_B$<u>cis</u> to Ar), 6.02 (2H, s, NH$_2$), 6.74 (1H, d, J 2.5 Hz, H-3 or H-5), 6.76 (1H, d, J 2.5 Hz, H-3 or H-5), 6.84 (1H, dd, J 17.5 and 11.0 Hz, CH). This was used to prepare the methyl 4-chloro-2-phenylacetamido-6-vinylbenzoate, as described above. $\delta_H$ (250 MHz, DMSO-$d_6$) 3.65 (2H, s, C$\underline{H}_2$-Ph), 3.66 (3H, s, CO$_2$C$\underline{H}_3$), 5.41 (1H, d, J 11 Hz, C$\underline{H}_A$H$_B$, H$_A$ trans to Ar), 5.88 (1H, d, J 17.5 Hz, CH$_A$$\underline{H}_B$, H$_B$ cis to Ar), 6.76 (1H, dd, J 17.5 Hz and 11 Hz, CH), 7.24–7.38 (5H, m, ArH), 7.57 (2H, m, H-3 and H-5), 9.93 (1H, s, NH).

Cyclisation of this amide afforded the title compound m.p. 240°–244° C. (from DMF/water); (Found: C, 68.61; H, 4.14; N, 4.79. C$_{17}$H$_{12}$ClNO$_2$ requires C, 68.58; H, 4.06; N, 4.70%); $\delta_H$ (DMSO-$d_6$) 5.27 (1H, dd, J 11.0 and 1.3 Hz, C$\underline{H}_A$H$_B$, H$_B$trans to Ar), 5.56 (1H, dd, J 17.3 and 1.3 Hz, C H$_A$$\underline{H}_B$, H$_A$cis to Ar), 7.16 (1H, d, J 2.1 Hz, H-6 or H-8), 7.29–7.43 (6H, m, ArH and H-6 or H-8), 7.71 (1H, dd, J 17.3 and 11.0 Hz, CH), 9.99 (1H, br s, OH), and 11.55 (1H, s, NH); m/z 297 (M$^+$).

EXAMPLE 36

7-Chloro-5-ethyl-4-hydroxy-3-phenyl-2(1H)-quinolone

A slurry of platinum on sulphide carbon (0.1 g) in ethyl acetate was added under nitrogen to a solution of the methyl 2-amino- 4-chloro-6-vinylbenzoate (0.362 g) in ethyl acetate. This mixture was hydrogenated at 30 psi for 2 h. The catalyst was filtered off and the solvent removed in vacuo to leave the desired methyl 2-amino-4-chloro-6-ethylbenzoate as a yellow oil (0.34 g). $\delta_H$ (250 MHz, DMSO-$d_6$) 1.08 (3H, t, J 7.5 Hz, CH$_2$C$\underline{H}_3$), 2.60 (2H, q, J 7.5 Hz, C$\underline{H}_2$CH$_3$), 3.81 (3H, s, CO$_2$CH$_3$), 5.85 (2H, s, NH$_2$), 6.46 (1H, d, J 2.5 Hz, H-3 or H-5), 6.65 (1H, d, J 2.5 Hz, H-3 or H-5).

Methyl 4-chloro-6-ethyl-2-phenylacetamido-benzoate was prepared in an analogous fashion to that described above. $\delta_H$ (DMSO-$d_6$) 1.12 (3H, t, J 7.5 Hz, CH$_2$C$\underline{H}_3$), 2.62 (2H, q, J 7.5 Hz, C$\underline{H}_2$—CH$_3$), 3.64 (5H, s, CO$_2$C$\underline{H}_3$ and C $\underline{H}_2$—Ph), 7.22–7.34 (6H, m, ArH and 3-H or 5-H), 7.48 (1H, d, J 2.5 Hz, 3-H or 5-H), 9.86 (1H, s, NH); m/z 332 ((M+1)$^+$)

This was cyclised to afford the title compound m.p. 284°–288° C. (from DMF/water); (Found: C, 67.88; H, 4.62; N, 4.60. C$_{17}$H$_{14}$ClNO$_2$ requires C, 68.12; H, 4.71; N, 4.67%); $\delta_H$ (DMSO-$d_6$) 1.20 (3H, t, J 7.3 Hz, CH$_2$C$\underline{H}_3$), 3.12 (2H, q, J 7.3 Hz, C$\underline{H}_2$—CH$_3$), 6.99 (1H, d, J 2.1 Hz, H-6 or H-8), 7.20 (1H, d, J 2.1 Hz, H-6 or H-8), 7.30–7.43 (5H, m, ArH), 9.83 (1H, br s, OH), and 11.49 (1H, s, NH); m/z 299 (M$^+$).

EXAMPLE 37

7-Chloro-5-ethyl-4-hydroxy-3-(3-phenoxyphenyl)-2-(1H)-quinolone

Large brownish yellow cubic crystals m.p. 222°–224° C. from ethyl acetate/hexane (Found: C, 70.30; H, 4.44; N, 3.30. C$_{23}$H$_{18}$ClNO$_3$ requires C, 70.50; H, 4.63; N, 3.57%); $\delta_H$ (360 MHz, DMSO-$d_6$) 1.21 (3H, t, J 7.4 Hz, CH3), 3.14 (2H, q, J 7.4 Hz, CH2), 6.97–6.99 (3H, m, Ar—H), 7.08–7.13 (4H, m, Ar—H), 7.22 (1H, d, J 2.2 Hz, Ar—H), 7.36–7.44 (3H, m, Ar—H), 9.75–10.0 (1H, v br s, OH), 11.35 (1H, br s, NH); m/z (EI$^+$) 391 (M$^+$).

EXAMPLE 38

5-Hydroxy-2-phenyl-7-trifluoromethyl-2(1H)-quinolone mp 310° C. (slow decomp, from MeOH/H$_2$O) (Found: C, 62.59; H, 3.04; N, 4.38; C$_{16}$H$_{10}$F$_3$NO$_2$ requires: C, 62.96; H, 3.30; N, 4.59%); $\delta_H$ (DMSO-$d_6$) 7.29–7.62 (7H, m, 6H, 8H and 5×ArH), 8.16 (1H, d, J 8.6 Hz, 5-H), 11.71 (1H, s, NH); m/z 305 (M$^+$).

EXAMPLE 39

7-Chloro-4-hydroxy-3-(3,benzoylbenzyl)-2(1H)-quinolone m-Tolylacetic acid (50 g) and N-bromosuccinimide (60 g) were refluxed in carbon tetrachloride (400 ml) for 3 h. The mixture was filtered, evaporated in vacuo, and the solid recrystallised from toluene and hexane to give 3-bromomethyl phenylacetic acid (28.6 g) as white needles. $\delta_H$ (250 MHz, DMSO-$d_6$) 3.63 (2H, s, CH$_2$CO), 4.28 (2H, s, CH$_2$Br), 7.1–7.7 (4H, m, ArH). Hydrogen chloride was bubbled through a solution of this acid (25 g) in methanol (500 ml) for 5 min, then the solution stood at room temperature for 1h, evaporated in vacuo, after (300 ml) added, and the solution washed with saturated sodium hydrogencarbonate, water and brine, dried, and evaporated in vacuo to give methyl 3-bromomethylphenylacetate (25 g) as an oil; $\delta_H$ (360 MHz, CDCl$_3$) 3.58 (2H, s, CH$_2$CO), 3.68 (3H, s, Me), 4.47 (2H, s, CH$_2$Br), 7.2–7.4 (4H, m, ArH). The ester (2.5 g) was added to sodium hydrogencarbonate (5 g) in dimethylsulphoxide (35 ml) at 120° C. After 20 min the mixture was cooled in an ice bath, diluted with water and extracted with ether (×3). The ethereal extracts were washed with water and brine, dried, evaporated in vacuo, and purified by flash chromatography eluting with hexane:ethyl acetate (4:1 v/v) to give methyl 3-formylphenylacetate (2.02 g) as an oil; $\delta_H$ (360 MHz, CDCl$_3$) 3.71 (5H, s, CH$_2$ and Me), 7.25–7.4 (2H, m, ArH), 7.8–7.85 (2H, m, ArH), 10.0(1H, s, CHO); m/z (EI$^+$) 178 (M$^+$). Phenyl magnesium bromide (1.9 ml, 3M in ether) was added to a solution of the aldehyde (1.02 g) in ether (20 ml) at–78° C. The mixture was warmed to room temperature, cooled to–78° C. and phenylmagnesium bromide (1.9 ml, 3M) added, then warmed to room temperature. The mixture was washed with saturated ammonium chloride solution, water and brine, dried and evaporated in vacuo to give an oil. Pyridinium chlorochromate (1 g) was added to the oil in dichloromethane (20 ml), and the mixture stirred for 1h. Ether (50 ml) was added, and the mixture filtered through silica gel then evaporated to give an oil (0.63 g). The oil was dissolved in THF (15 ml) and lithium hydroxide (6 ml, 0.5H in water) added. After 1h ether and water were added, the mixture separated, and the aqueous layer acidified with 1N HCl, then extracted with ethyl acetate (×3). The ethyl acetate was washed with water and brine, dried and evaporated in vacuo to give 3-benzoylphenylacetic acid (310mg) as white plates. m.p. 101°–103° C.; $\delta_H$ (250 MHz, CDCl$_3$) 3.76 (2H, s, CH$_2$), 7.4–7.9 (9H, m, ArH); m/z (EI$^+$) 240 (M$^+$). The acid was converted in the standard way to give the title compound as pale yellow plates. m.p. 294°–295° C. (from dimethylformamide/water); (Found: C, 68.94;H, 3.91;N, 3.60. C$_{22}$H$_{14}$NO$_3$Cl +0.4 H2O requires C, 68.98;H, 3.89;N, 3.65%); $\delta_H$ (360 MHz, DMSO-$d_6$) 7.31 (1H, dd, J 8.7 and 2.0 Hz, H-6), 7.32(1H, d, J 2.0 Hz, H-8), 7.5–7.9 (9H, m, ArH), 7.96(1H, d, J 8.7 Hz, H-5), 10.6(1H, s, OH), 11.6(1H, s, NH); m/z (EI$^+$) 375 (M$^+$).

EXAMPLE 40

7-Chloro-4-hydroxy-3-[3-(3-thiophenecarbonyl)-phenyl]-2(1H)quinolone

White amorphous solid, m.p. 287°–290° C. (from dimethylformamide/acetone/water) (Found: C, 63.02;H, 2.94;N, 3.59. C$_{20}$H$_{12}$NO$_3$SCl requires C, 62.91;H, 3.17;N, 3.67%);

$\delta_H$ (360 MHz, DMSO-d$_6$) 7.24(1H, dd, J 2.0 and 8.6 Hz, H-6), 7.35 (1H, d, J 2.0 Hz, H-8), 7.55–7.65 (2H, m), 7.65–7.8 (3H, m), 7.84 (1H, d, J 1 Hz, H-2'), 7.96(1H, d, J 8.6 Hz, H-5), 8.30(1H, dd, J 1 and 2 Hz, thiophene H-2), 10.6(1H, br s), 11.82(1H, s); m/z (EI$^+$) 381 (M$^+$).

EXAMPLE 41

7-Chloro-4-hydroxy-3-[3-(3-furanylcarbonyl)phenyl]-2(1H)-quinolone

Tan amorphous solid, m.p. 284°–286° C. (Found: C, 64.98;H, 3.29;N, 3.69. C$_{20}$H$_{12}$NO$_4$Cl +0.2H$_2$O requires C, 65.03;H, 3.38; N, 3.79%); $\delta_H$ (360 MHz, DMSO-d$_6$) 6.94(1H, d, J 1.5 Hz, furan H-4), 7.24(1H, dd, J 1.3 and 6.7 Hz, H-6), 7.34(1H, d, J 1.3 Hz, H-8), 7.59(1H, t, J8 Hz, H-5'), 7.74(1H, d with other fine coupling, J 8 Hz, H-4' or H-6'), 7.77(1H, d, with other fine coupling, J 8 Hz, H-6' or H-4'), 7.90–7.9 (2H, m, H-2' and furan H- 5), 7.99(1H, d, J 6.7 Hz, H-5), 8.41(1H, s, furan H-2), 10.6(1H, br s), 11.62(1H, s); m/z (CI$^+$, NH$_3$) 366 (M$^+$+H).

EXAMPLE 42

7-Chloro-4-hydroxy-3-[3-(1-pyrrolemethyl)phenyl]-2(1H)-quinoline

Oxalyl chloride (15.2 ml) was added to a solution of 3-bromomethylphenyl acetic-acid (20 g) and dimethylformamide (4 drops) in dichloromethane (350 ml) at room temperature. After 1h the solution was evaporated in vacuo then methyl 4-chloroanthranilate (10.6 g) and dichloroethane (300 ml) added, and the mixture refluxed for 35 rain, then cooled, the mixture washed with sodium hydrogen carbonate solution and brine, dried, evaporated in vacuo, and recrystallised from ethyl acetate/hexane to give methyl 2-(3-bromethylphenylacetamido)-4-chlorobenzoate as a white solid; $\delta_H$(360 MHz, CDCl$_3$) 3.75 (2H, s, CH$_2$CO), 3.86 (3H, s, Me), 4.50 (2H, s, CH$_2$Br), 7.03(1H, dd, J 8.7 and 1.90 Hz, H-5), 7.2–7.4 (4H, m, ArH), 7.91(1H, d, J 8.7 Hz, H-6), 8.80(1H, d, J 1.9 Hz, H-3), 11.15(1H, s, NH); m/z (EI$^+$) 397 (M$^+$). Potassium hexamethyldisilazide (22 ml, 0.5M in toluene) was added to a solution of pyrrole (0.74 g) in THF (20 ml) at –78° C., warmed to room temperature, then recooled to –30° C. The above amide (2 g) in THF (20 ml) was added, the solution kept at –30° C. for 1h, then saturated ammonium chloride added. The mixture was diluted with ethyl acetate, separated and the organic layer washed with water and brine, dried, evaporated in vacuo and purified by flash chromatography, eluting with hexane:ethyl acetate (5:1 v/v) to give methyl 2-[3-(1-pyrrole methyl)phenylacetamido]-4-chlorobenzoate; $\delta_H$ (360 MHz, CDCl$_3$) 3.65 (2H, s, CH$_2$CO), 3.86 (3H, s, Me), 5.08 (2H, s, CH$_2$N), 6.16 (2H, t, J 2 Hz, pyrrole H-3), 6.69 (2H, t, J 2 Hz, pyrrole H-2), 7.0–7.3 (5H, m, ArH), 7.91(1H, d, J 8.4 Hz, CHCCO), 8.8 (1H, s, CHCN), 11.1 (1H, s, NH). This was cyclised in the normal way to give the final compound as a white solid, m.p. >300° C. (from dimethylformamide/water); (Found: C, 68.35;H, 4.03;N, 8.23. C$_{20}$H$_{15}$N$_2$O$_2$Cl requires C, 68.48;H, 4.31;N, 7.99%); $\delta_H$ (250 MHz, DMSO-d$_6$) 5.11 (2H, s, CH$_2$), 6.01 (2H, t, J 2 Hz, pyrrole H-3), 6.86 (2H, t, J 2 Hz, pyrrole H-2), 7.1–7.4 (6H, m, ArH), 7.96 (1H, d, J 9 Hz, H-5), 10.3(1H, s, OH), 11.52(1H, s, NH).

EXAMPLE 43

7-Chloro-4-hydroxy-3-[3-(1-indolemethyl)phenyl]-2(1H)quinolone

White granular solid, m.p. 285°–287° C. (from dimethyl formamide/water) (Found: C, 72.08;H, 4.23;N, 7.11. C$_{24}$H$_{17}$N$_2$O$_2$Cl requires C, 71.91;H, 4.28;N, 6.99%); $\delta_H$ (360 MHz, DMSO-d$_6$) 5.43 (2H, s, CH$_2$), 6.47(1H, d, J 4.2 Hz, indole H-3), 7.00 (1H, t, J 7.1 Hz), 7.08–7.12 (2H, m), 7.21(1H, dd, J 2.1 and 8.6 Hz, H-6), 7.24–7.31 (3H, m), 7.34–7.55 (4H, m), 7.91.(1H, d, J 8.6 Hz, H-5), 10.3 (1H, br s, OH), 11.51 (1H, s, NH); m/z (EI) 400 (M$^+$).

EXAMPLE 44

7-Chloro-4-hydroxy-3-[3-(3-thiophenemethyl)phenyl]-2(1H)-quinolone n-Butyllithium (92 ml, 1.6M in hexane, 147 mmol) was added to a solution of 3-bromothiophene (24 g, 147 mmol) in ether (200 ml) at–78° C. over 10 min. After 30 min the mixture was cannulated into a solution of methyl 3-formylphenylacetate (20 g, 113 mmol) in ether (200 ml) at –78° C., then the mixture warmed to room temperature. The mixture was washed with water, and brine, dried, evaporated in vacuo, and purified by flash chromatography, eluting with hexane:ethyl acetate (5:2 v/v) to give methyl 3-(3-thiophenehydroxymethyl)phenylacetate (17.4 g) as an oil; $\delta_H$ (360 MHz, CDCl$_3$) 3.50 (2H, s, CH$_2$), 3.66 (3H, s, Me), 5.87 (1H, s, CHO), 6.9–7.3 (7H, m, ArH). The oil was dissolved in dichloromethane (200 ml) with triethylsilane (20.8 ml), cooled to 0° C., and trifluoroacetic acid (10 ml) added. After 45 min the solution was washed with saturated sodium hydrogencarbonate solution, water, and brine, dried, evaporated in vacuo, and purified by flash chromatography, eluting with hexane:ethyl acetate (8:1 v/v) to give methyl 3-(3-thiophenemethyl)phenylacetate (9.4 g) as an oil; $\delta_H$ (360 MHz, CDCl$_3$) 3.54 (2H, s, CH$_2$CO), 3.68 (3H, s, Me), 3.88 (2H, s, ArCH$_2$Ar), 6.8–7.3 (7H, m, ArH). This was taken through in the normal way to give the title compound (4.10 g) as very light yellow needles; m.p. 320°–322° C. (from dimethylformamide); (Found: C, 64.96;H, 3.82;N, 4.17. C$_{20}$H$_{14}$ClNO$_2$S requires C, 65.30;H, 3.83;N, 3.81%); $\delta_H$ (360 MHz, DMSO-d$_6$) 3.96 (2H, s, CH$_2$), 6.99 (1H, d, J 8.5 Hz, thiophene H-4), 7.1–7.3 (7H, m, ArH), 7.43 (1H, dd, J 3.0 and 8.5 Hz, thiophene H-5), 7.91 (1H, d, J 8.6 Hz, H-5), 10.2(1H, s, OH), 11.49(1H, s, NH); m/z (EI$^+$) 367 (M$^+$).

EXAMPLE 45

7-Chloro-4-hydroxy-3-[3-(4-methoxymethylbenzyl)-phenyl]-2(1H)-quinolone

4-Bromobenzylalcohol(5.0 g, 26.7 mmol) was dissolved in THF (130 ml) and methyl iodide added (6.7 ml, 107.0 mmol). Sodium hydride (1.20 g of 80% dispersion in oil, 40.1 mmol) was added in two portions while stirring at room temperature under nitrogen. After stirring for 2 hours, the solvents were removed in vacuo and the residue partitioned between water and ether. The water was reextracted with ether and the combined organic fractions were then washed with water and brine before drying (Na$_2$SO$_4$) and evaporating in vacuo to give 4-bromobenzylmethyl ether as an orange liquid (5.3 g, 26.4 mmol). $\delta_H$ (250 MHz, CDCl$_3$) 3.39 (3H, s, CH$_3$), 4.40 (2H, s, CH$_2$), 7.21 (2H, d, J 7.5 Hz, Ar—H), 7.48 (2H, d, J 7.5 Hz, Ar—H).

The bromobenzylmethyl ether (2.28 g, 11.35 mmol) was dissolved in anhydrous ether (40 ml) and cooled to −78° C. with stirring under nitrogen. tert-Butyllithium (13.4 ml of a 1.7M solution in pentane, 22.7 mmol) was added dropwise over 5 mins, and stirring continued for 45 mins. This mixture was then cannulated into a suspension of pentynyl copper (1.48 g, 11.35 mmol) in anhydrous ether (40 ml) at −78° C. and allowed to warm to −40° C., with stirring under nitrogen. Light was excluded with aluminium foil. After 15 mins methyl 2-(3-bromomethylphenylacetamido)-4-chlorobenzoate (1.5 g, 3.78 mmol) was added as a solution in anhydrous THF (10 ml). The mixture was swirled manually as necessary. After stirring at −40° C. for 1.5 hours, the reaction was allowed to warm to room temperature and stirred for a further 1 hour. Saturated ammonium chloride solution was added and the mixture filtered through celite to remove copper residues. The organic layer was separated and washed with water and brine before drying ($Na_2SO_4$) and evaporating in vacuo to give a yellow oil. This was purified by flash chromatography eluting with 15% ethyl acetate in hexane to give methyl 2-[3-(4-methoxymethylbenzyl)phenyl acetamido]-4-chlorobenzoate as a clear colourless oil (0.81 g, 1.85 mmol); $\delta_H$ (360 MHz, $CDCl_3$) 3.36 (3H, s, $CH_2OCH_3$), 3.71 (2H, s, $NHCOCH_2$), 3.84 (3H, s, $COOCH3$), 3.99 (2H, s, $ArCH_2Ar$), 4.41 (2H, s, $ArCH_2O$), 7.03 (1H, dd, J 8.6 and 2.1 Hz, 5-H), 7.10(1H, d, J 7.5 Hz, Ar—H), 7.16–7.30 (7H, m, Ar—H), 7.91(1H, d, J 8.6 Hz, 6-H), 8.81(1H, d, J 2.1 Hz, 3-H), 11.06(1H, br s, NH); m/z ($EI^+$) 437 ($M^+$).

The acetamide ester was cyclised in the usual way to give the title compound as a white amorphous solid m.p. 276°–278° C. (DMF/Acetone/Water) (Found: C, 71.35;H, 4.87;N, 3.37. $C_{24}H_{20}ClNO_3$ requires C, 71.20;H, 4.73;N, 3.46%) δ(360 MHz, DMSO-$d_6$), 3.25 (3H, s, $CH_3$), 3.96 (2H, s, $ArCH_2Ar$), 4.35 (2H, s, $ArCH_2O$), 7.14–7.33 (10H, m, 8×Ar—H, 6-H and 8-H), 7.92 (1H, d, J 8.6 Hz, 5-H), 10.0–10.4(1H, vbr s, OH), 11.50(1H, br s, NH); m/z ($EI^+$) 450 ($M^+$).

EXAMPLE 46

7-Chloro-4-hydroxy-3-(3-benzylphenyl)-(1H)-quinolone

White amorphous solid, m.p. 304°–306° C. (from dimethylformamide/water) (Found: C, 71.43;H, 4.42;N, 3.46%). $C_{22}H_{16}NO_2Cl$ +0.5$H_2O$ requires C, 71.26;H, 4.62;N, 3.77%); $\delta_H$ (360 MHz, DMSO-$d_6$) 3.96 (2H, s, $CH_2$), 7.1–7.4 (11H, m, ArH), 7.92(1H, d, J 8.6 Hz, H-5), 10.2(1H, s, OH), 11.50(1H, s, NH); m/z ($CI^+$, $NH_3$) 362 ($\underline{M}^++H$).

EXAMPLE 47

7-Chloro-4-hydroxy-3-[3-(4-methylthiobenzyl)phenyl]-2(1H)-quinolone

White amorphous solid, m.p. 296°–297° C. (from dimethylformamide/water) (Found: C, 67.85;H, 4.42;N, 3.44. $C_{23}H_{18}NO_2SCl$ requires C, 67.72;H, 4.45;N, 3.43%); δ (DMSO-$d_6$) 2.43 (3H, s, Me), 3.92 (2H, s, $CH_2$), 7.1–7.3 (10H, m, ArH), 7.92(1H, d, J 8.7 Hz, H-5), 10.1(1H, br s, OH), 11.51(1H, s, NH); m/z ($EI^+$) 407 ($\underline{M}^+$).

EXAMPLE 48

7-Chloro-4-hydroxy-3-[3-(4-methoxymethoxybenzyl)phenyl]-2(1H),quinolone

Amorphous white solid, m.p. 261°–264° C. (from DMF/Acetone/$H_2O$) (Found: C, 68.72;H, 4.88;N, 3.33. $C_{24}H_{20}ClNO_4$ requires C, 68.33;H, 4.78;N, 3.32%); δ (360 MHz, DMSO-$d_6$) 3.35 (3H, s, $CH_3$), 3.90 (2H, s, $ArCH_2Ar$), 5.13 (2H, s, $OCH_2O$), 6.93 (2H, d, J 8.6 Hz, 3"-H), 7.13–7.22 (6H, m, 6×Ar—H), 7.28–7.32 (2H, m, 2×Ar—H), 7.92(1H, d, J 8.6 Hz, 5-H), 10.0–10.3(1H, v br s, OH), 11.51(1H, br s, NH); m/z ($EI^+$) 421 ($M^+$).

EXAMPLE 49

7-Chloro-4-hydroxy-3-[3-(4-hydroxybenzyl)phenyl]-2(1H)-quinolone

Tan amorphous solid, m.p. 288°–292° C. (from dimethylformamide/acetone/water) (Found: C, 68.76;H, 4.37;N, 3.69. $C_{22}H_{16}NO_3Cl$ +0.3$H_2O$ requires C, 68.95;H, 4.37;N, 3.66%); $\delta_H$ (360 MHz, DMSO-$d_6$) 3.84 (2H, s, $CH_2$), 6.66 (2H, d, J 8.4 Hz, H-3"), 7.04 (2H, d, J 8.4 Hz, H-2"), 7.11 (1H, d, J 7 Hz), 7.17 (1H, d, J 7 Hz), 7.18 (1H, s, H-2'), 7.20(1H, dd, J 8.6 and 1.8 Hz, H-6), 7.29 (1H, t, J 7 Hz, H-5'), 7.31(1H, d, J 1.8 Hz, H-8), 7.91 (1H, d, J 8.6 Hz, H-5), 9.14(1H, s, OH), 10.21(1H, br s, NH), 11.50 (1H, s, OH); m/z ($CI^+$, $NH_3$) 378 ($M^++H$).

EXAMPLE 50

7-Chloro-4-hydroxy-3-[3-(4-(N-morpholine-2-ethyl)benzyl) phenyl)-2-(1H)-quinolone 1-Pentynyl copper (6.61 g, 50.6 mmol) was used to couple TBDMS protected 4-bromophenethyl alcohol (15.89 g, 50.4 mmol) and methyl 4-chloro-2-(3-bromomethylphenylacetamido)benzoate (6.68 g, 16.9 mmol) as described above. Flash chromatography (5% ethyl acetate/hexane) gave methyl 4-chloro-2-[3-(4-(tert-butyldimethylsilyloxy- 2-ethyl)benzyl)-phenylacetamido]benzoate as a yellow oil (8.02 g); $\delta_H$ (250 MHz, $CDCl_3$) 0.02 (6H, s, $OSiCH_3CH_3$), 0.88 (9H, s, $^tBu$), 2.80 (2H, t, J 7.0 Hz, $ArCH_2CH_3$), 3.74 (2H, s, $ArCH_3CONH$), 3.80 (2H, t, J 7.0 Hz, $CH_2OSi$), 3.87 (3H, s, $CO_2Me$), 3.99 (2H, s, $ArCH_2Ar$), 7.02–7.32 (9H, m, $ArCH_2Ar$ and 5-H), 7.92 (1H, d, J 8.4 Hz, 6-H), 8.85 (1H, d, J 2.8 Hz, 3-H), 11.07(1H, br s, NH); m/z ($EI^+$) 552 ($M^+$).

The amide (8.02 g, 14.54 mmol) was dissolved in a mixture of dry methanol (60 ml) and dry dichloromethane (10 ml). Dowex 50 W×8 acid ion exchange resin (which had been washed with methanol and dried at the pump, 16 g) was then added to this solution and the mixture stirred at room temperature under nitrogen for 16 hours. The Dowex was filtered off and the filtrate concentrated in vacuo. The product was isolated by flash chromatography (2% methanol/dichloromethane) to give methyl 4-chloro-2-[3-(4-(2-hydroxyethyl)-benzyl)phenylacetamido]benzoate as a viscous yellow oil (5.38 g); $\delta_H$ (250 MHz, $CDCl_3$) 2.83 (2H, d, J 6.5 Hz, $ArCH_2CH_2$), 3.71 (2H, s, $ArCH_2CONH$), 3.84 (2H, t, J 6.5 Hz, $ArCH_2CH_2OH$), 3.84 (3H, s, $CO_2Me$), 3.97 (2H, s, $ArCH_2Ar$), 7.03 (1H, dd, J 8.6 and 2.1 Hz, 5-H), 7.10–7.32 (8H, m, $ArCH_2Ar$), 7.91(1H, d, J 8.6 Hz, 6-H), 8.82(1H, d, J 2.1 Hz, 3-H), 11.06 (1H, br s, NH); m/z ($EI^+$) 438 ($M^+$).

This alcohol was mesylated by addition of methane sulphonylchloride (0.186 ml, 2.40 mmol) to a solution of the alcohol (1.017 g, 2.32 mmol) and triethylamine (0.48 ml, 3.44 mmol) in a mixture of dry diethylether (10 ml) and dry tetrahydrofuran (4 ml) under nitrogen at 0° C. The reaction was allowed to warm to room temperature and stirred for 30 mins before filtering off the white precipitate of triethylamine hydrochloride and concentrating the filtrate in vacuo to yield the mesylated intermediate as a colourless oil.

This oil was dissolved in a mixture of dry methanol (5 ml) and dry dichloromethane (2 ml). Morpholine (4 ml, 45.87 mmol) was introduced to the solution at room temperature under nitrogen and the reaction stirred for 24 hrs before concentrating in vacuo. The residue was taken up in ethyl acetate, washed with saturated sodium bicarbonate solution, water and brine, then dried (MgSO$_4$). The organics were concentrated in vacuo to leave a yellow oil which was purified by flash chromatography (2% methanol/dichloromethane)to yield methyl 4-chloro-2-[3-(4-(N-morpholine-2-ethyl)benzyl)phenylacetamido]benzoate as a colourless oil (0.417 g); $\delta_H$ (250 MHz, CDCl$_3$) 2.53–2.61 (6H, m, N CH$_2$CH$_2$O and NCH$_2$CH$_2$Ar), 2.74–2.80 (2H, m, NCH$_2$ CH$_2$Ar), 3.71 (2H, s, ArCH$_2$CONH), 3.75 (4H, t, J 4.7 Hz, OCH$_2$CH$_2$N), 3.84 (3H, s, CO$_2$Me), 3.96 (2H, s, Ar CH$_2$Ar), 7.03 (1H, dd, J 8.7 and 2.1 Hz, 5-H), 7.07–7.31 (8H, m, ArCH$_2$Ar), 7.91 (1H, d, J 8.7 Hz, 6-H), 8.82(1H, d, J 2.1 Hz, 3-H), 11.06 (1H, br s. NH); m/z 507 (EI$^+$) M$^+$.

The above amide was cyclised under the standard conditions. The reaction was quenched with methanol and concentrated in vacuo to leave a yellow gum. The residue was partitioned between ethyl acetate and 2N sodium hydroxide solution. The aqueous fraction was acidified with 2N hydrochloric acid to pill and the resultant emulsion reduced (but not to dryness) in vacuo. The resultant suspension was filtered and the solid washed with water before drying at the pump to leave an off white solid. This solid was crystallised from methanol to give the title compound as white plates; m.p. 273°–276° C. (from MeOH); (Found: C, 65.86;H, 5.54;N, 5.38. C$_{28}$H$_{27}$ClN$_2$O$_3$.HCl requires C, 65.76;H, 5.52;N, 5.48%); $\delta_H$ (360 MHz, 80° C., DMSO-d$_6$) 2.94°–3.10 (6H, m, NCH$_2$CH$_2$O and NCH$_2$CH$_2$Ar), 3.10–3.30 (2H, m, NCH$_2$CH$_2$Ar), 3.84–3.94 (4H, m, NCH$_2$CH$_2$O), 3.97 (2H, s, ArCH$_2$Ar), 7.14–7.33 (9H, m, ArCH$_2$Arand 6-H), 7.38(1H, d, J 2.0 Hz, 8-H), 7.95(1H, d, J 8.6 Hz, 5-H), 11.52(1H, s, NH); m/z (M$^+$+H) 475 (CI$^+$).

EXAMPLE 51

6,7-Dichloro-4-hydroxy-3-phenyl-2(1H)-quinolone

White needles; mp 347°–349° C. (from DMSO); (Found: C, 58.29; H, 2.81;N, 4.35. C$_{15}$H$_9$Cl$_2$NO2.0.1H$_2$O requires C, 58.50;H, 3.01;N, 4.55%); $\delta_H$ (360Mhz, DMSO-d$_6$) 7.29–7.42 (5H, m, Ph), 7.48 (1H, s, 5-H or 8-H), 8.11 (1H, s, 5-H or 8-H), 11.62 (1H, s, NH;m/z (EI$^+$) 305 (M$^+$).

EXAMPLE 52 cis 7-Chloro-4-hydroxy-3-(4-phenylethenylphenyl)-2(1H) quinolone

4-Bromomethylphenylacetic acid (20 g, 8.7 mmol) was suspended in toluene (300 ml). Triphenylphosphine (45 g, 170 mmol) was added and the mixture heated at reflux for 16 hours giving a thick white precipitate. This solid was collected by filtration, washing with ether×3, and dried under high vacuum to give 4-triphenylphosphinemethylphenylacetic acid bromide (42 g, 86 mmol); $\delta_H$ (250 MHz, DMSO-d$_6$) 3.52 (2H, s, CH$_2$COOH), 5.12 (2H, d, J 15 Hz, CH$_2$P), 6.92 (2H, dd, J 8 and 2 Hz, PCH$_2$CCH), 7.12 (2H, d, J 8 Hz, HOOCCH$_2$CCH), 7.61–7.79 (12H, m, Ph-H), 7.90 (3H, dt, J 7 and 2 Hz, PPh(4)H). The phosphonium salt (40 g, 81.5 mmol) was suspended in anhydrous THF (300 ml) and diisopropylamine (35.4 ml, 187 mmol) added. The mixture was cooled to −78° C. and n-butyl lithium (70 ml of a 2.5M solution in hexanes, 175 mmol) was slowly added maintaining the temperature of the mixture at <−60° C. A colour change to brown through yellow and orange was observed. The reaction vessel was warmed to 0° C. and stirred for 30 mins. After recooling to −78° C., freshly distilled benzaldehyde (10.4 g, 97.8 mmol) was added whereupon the colour faded to orange. The reaction was stirred for 30 mins before being allowed to warm to room temperature for a further 30 mins and changing colour to yellow. The mixture was evaporated in vacuo to 100 ml then diluted with ethyl acetate and washed with water and brine, dried (Na$_2$SO$_4$) and evaporated to give a white solid. The solid was extracted with hot toluene and hot ether. Combined organic extracts were evaporated in vacuo. The residue (20.5 g) was dissolved in methanol (250 ml) and cooled to 0° C. Hydrogen chloride gas was bubbled through the solution for 5 mins then the mixture was stirred at room temperature under nitrogen for 16h. The solid formed was removed by filtration. The filtrate was evaporated, swilled with ether, refiltered and reduced in vacuo. The residue was separated by dry flash chromatography eluting with 0%–8% ethyl acetate in hexane to give a mixture of cis and trans methyl 4-stilbene acetates (3.9 g). This mixture was separated by flash chromatography eluting with 6% ethyl acetate/hexane to give stereoisomer A (1.45 g) and stereoisomer B (1.25 g). Isomer A (1.0 g, 4.0 mmol)was dissolved in THF (15 ml) and water (10 ml). Lithium hydroxide (9.52 ml of a 0.5M solution, 4.8 mmol) was added and the mixture stirred at room temperature for 45 mins. The THF was removed in vacuo and the aqueous residue partitioned between ether and sodium hydroxide solution. The aqueous fraction was retained and acidified to pH 1 (hydrochloric acid) giving a white precipitate which was extracted into ethyl acetate×2. The combined organic fractions were washed with water and brine before drying (Na$_2$SO$_4$) and evaporating in vacuo to give cis 4-stilbene acetic acid as a clear colourless oil (0.95 g, 4.0 mmol). $\delta_H$ (360 MHz, DMSO-d$_6$) 3.52 (2H, s, CH$_2$), 6.59 (1H, d, J 12.4 Hz, ArCH:CHAr), 6.64 (1H, d,J 12.4 Hz, ArCH:CHAr), 7.11–7.30 (9H, m, Ar—H); m/z (EI$^+$) 238 (M$^+$). [Isomer B was treated with lithium hydroxide as described for isomer A to give trans 4-stilbene acetic acid. $\delta_H$ (250 MHz, DMSO-d$_6$) 7.14(1H, d, J 15.5 Hz, ArC H:CHAr)]. Isomer A was taken through to give the title compound as a buff coloured amorphous solid; m.p. 284°–286° C. (from dimethylformamide/acetone/water) (Found: C, 73.80;H, 3.97;N, 3.69. C$_{23}$H$_{16}$ClNO$_2$ requires C, 73.90;H, 4.31;N, 3.75%); $\delta_H$ (360 MHz, DMSO-d$_6$) 6.64 (2H, s, ArCH:CHAr), 7.20–7.35 (11H, m, Ar—H, 6-H and 8-H), 7.93(1H, d, J 8.7 Hz, 5-H), 10.1–10.5(1H, v br s, OH), 11.53(1H, br s, NH); m/z (EI$^+$) 273 (M$^+$).

EXAMPLE 53 trans-7-Chloro-4-hydroxy-3-(3-phenylethenylphenyl)-(1H)-quinolone

White needles, m.p. 320°–324° C. (from dimethylformamide/water) (Found: C, 73.66;H, 4.35;N, 3.68. C$_{23}$H$_{16}$NO$_2$Cl requires C, 73.90;H, 4.31;N, 3.75%); $\delta$ (360 MHz, DMSO-d$_6$) 7.2–7.7 (13H, m, ArH and CH=CH), 7.94 (1H, d, J 8.7 Hz, H-5), 10.33 (1H, s, OH), 11.6 (1H, s, NH); m/z (CI$^+$, NH$_3$) 374 (M$^+$+H).

EXAMPLE 54 cis-7-Chloro-4-hydroxy-3-(phenylethenylphenyl)-2(1H)-quinolone.

Tan amorphous solid, m.p. 247°–249° C. (from methanol) (Found: C, 72.98;H, 4.30;N, 3.71. C$_{23}$H$_{16}$NO$_2$Cl +0.2H$_2$O requires C, 73.19;H, 4.38;N, 3.71%); $\delta$ (360 MHz, DMSO- $d_6$) 6.60(1H, d, J 12.6 Hz, C$\underline{H}_A$=CH$_B$), 6.64 (1H, d, J 12.6 Hz, CH$_A$=C$\underline{H}_B$), 7.1–7.5 (11H, m, ArH), 7.92 (1H, d, J 8.7 Hz, H-5), 10.3 (1H, s, OH), 11.5 (1H, s, NH); m/z (CI$^+$, NH$_3$) 374 ($\underline{M}^+$+H).

EXAMPLE 55

7-Chloro-4-hydroxy-3-[3-(3-indolemethyl)phenyl]-2(1H) quinolone

Indole (2.53 g, 21.6 mmol) was dissolved in anhydrous THF (100 ml) and ethyl magnesium bromide (7.2 ml of a 3M solution in ether, 21.6 mmol) was added with care while stirring under nitrogen at room temperature. After stirring for 30 mins, the mixture was heated to reflux for 2 hours. On cooling methyl 3-bromomethylphenylacetate (3.33 ml, 20.6 mmol) was added and the reaction stirred at room temperature under nitrogen for 72 hours. The solvent was removed by rotary evaporation and the residue redissolved in ethyl acetate, washed with citric acid (0.5 M), saturated sodium bicarbonate solution and brine before drying (Na$_2$SO$_4$) and evaporating. The product was partly purified by flash chromatography eluting with 15% ethyl acetate in hexane to give an orange oil (750 mg). The oil (740 mg) was dissolved in THF (12 ml) and water (6 ml), 0.5M lithium hydroxide solution (6.37 ml, 3.18 mmol) was added and the reaction stirred at room temperature for 2 hours. The THF was removed in vacuo and the aqueous residue partitioned between ether and sodium hydroxide solution. The organic layer was reextracted with alkali and the combined aqueous fractions were acidified (pH 1, hydrochloric acid). The precipitate was extracted into ethyl acetate (×2). The organic fractions were washed with water and brine before drying (Na$_2$SO$_4$) and removing the solvent in vacuo to give 3-indole methyl phenylacetic acid as an oil (571 mg, 2.15 mmol); $\delta_H$ (250 MHz, DMSO-d$_6$) 3.49 (2H, s, ArC$\underline{H}_2$COOH), 4.01 (2H, s, ArCH$_2$Ar), 6.91 (1H, t, J 7.5 Hz, Ar—H), 7.01–7.22 (6H, m, Ar—H), 7.33 (1H, d, J 8.0 Hz, Ar—H), 7.42(1H, d, J 7.5 Hz, Ar—H); m/z (EI$^+$) 265 (M$^+$). This was taken through in the normal way to give the final compound as an orange amorphous solid m.p. 293°–295° C. (from methanol/water) (Found: C, 68.95;H, 4.33;N, 6.35. C$_{24}$H$_{17}$ClN$_2$O$_2$.H$_2$O requires C, 68.82;H, 4.57;N, 6.69%); $\delta_H$ (360 MHz, DMSO-d$_6$) 4.06 (2H, s, CH$_2$), 6.93 (1H, d, J 7.2 Hz, indole 6-H or indole 7-H), 7.04 (1H, t, J 7.5 Hz, indole 6-H or indole 7-H), 7.13–7.34 (8H, m, Ar—H), 7.51 (1H, d, J 7.8 Hz, Ar—H), 7.91 (1H, d, J 8.7 Hz, 5-H), 10.15–10.3(1H, br s, OH), 10.81 (1H, br s, NH), 11.50 (1H, br s, NH); m/z (EI$^+$) 400 (M$^+$).

EXAMPLE 56

7-Bromo-4-hydroxy-3-phenyl-2(1H)-quinolone

White needles; mp 343°–345° C. (from DMF); (Found: C, 56.71;H, 3.21;N, 4.40. C$_{15}$H$_{10}$BrNO$_2$ requires C, 56.99;H, 3.19;N, 4.43%); $\delta_H$ (360 MHz, DMSO-d$_6$), 7.29–7.42 (6H, m, Ph and 6-H), 7.47 (1H, d, J 1.8 Hz, 8-H), 7.86 (1H, d, J 8.6 Hz, 5-H), 10.29 (1H, br s, OH), 11.52 (1H, s, NH); m/z (EI$^+$) 315 M$^+$.

EXAMPLE 57

7-Chloro-4-hydroxy-3-[3-(2-pyridyloxy)phenyl]-2(1H)-quinolone

A catalytic quantity of concentrated sulphuric acid (1.0 ml) was added to a solution of (3-hydroxy)phenylacetic acid (17.38 g, 0.114 mol) in methanol (100 ml). The reaction mixture was stirred for 3 hours at room temperature and then concentrated in vacuo. The residue was partitioned between diethyl ether (200 ml) and a saturated aqueous solution of sodium hydrogen carbonate (200 ml). The ether phase was separated and washed with non-saturated sodium hydrogen carbonate solution (200 ml) and saturated brine solution (100 ml). The ether extract was dried over magnesium sulphate. The solvent was evaporated and the residue dried to afford methyl 3-hydroxyphenylacetate as an amber oil (18.61 g, 98%); $\delta_H$ (360 MHz, CDCl$_3$) 3.58 (2H, s, CH$_2$), 3.70 (3H, s, COOCH$_3$), 5.54 (1H, br s, OH), 6.74 (2H, m, ArH), 6.81 (1H, d, J 8 Hz, ArH), 7.17 (1H, t, J 8 Hz, ArH).

2-Bromopyridine (1.1 ml, 11.5 mmol) and potassium carbonate (2.76 g, 20.0 mmol) were added to a solution of methyl 3-hydroxyphenylacetate (1.66 g, 9.99 mmol) in anhydrous pyridine (12 ml). The vigorously stirred reaction mixture was heated to 90° C. under a nitrogen atmosphere and then copper (II) oxide (1.99 g, 25.0 mmol) was added under a positive nitrogen flush. The reaction mixture was heated under reflux for 16 hours, allowed to cool and diluted with dichloromethane. The mixture was filtered through hyflo and concentrated in vacuo. The residue was purified by flash chromatography on silica eluting with 1:3 ethyl acetate/petrol (60°–80° ) then 1:2 ethyl acetate/petrol (60°–80° ) to give methyl [3-(2-pyridyloxy)phenyl]acetate as a pale straw-coloured oil (1.85 g, 78%); $\delta_H$ (360 MHz, CDCl$_3$) 3.63 (2H, s, CH$_2$), 3.69 (3H, s, COOCH$_3$), 6.90 (1H, d, J 8 Hz, ArH), 6.99(1H, m, ArH), 7.06 (2H, m, ArH), 7.11 (1H, d, J 8 Hz, ArH), 7.34 (1H, t, J 8 Hz, 5'-H), 7.67 (1H, m, ArH), 8.19 (1H, m, 6"-H), m/z 243 (M$^+$).

Potassium bis(trimethylsilyl)amide in toluene (0.5M, 10.8 ml, 5.4mmol) was added dropwise to a solution of methyl [3-(2-pyridyloxy)phenyl]acetate (0.52 g, 2.14 mmol) and methyl 2-amino-4-chlorobenzoate (0.43 g, 2.32 mmol) in dry THF (30 ml). The reaction mixture was stirred at room temperature for 3 1hours then methanol (10 ml) was added. The solution was concentrated in vacuo, the residue was dissolved in 0.5M sodium hydroxide (25 ml) and washed with diethyl ether (2×25 ml). The aqueous phase was acidified with 5M hydrochloric acid. The resultant precipitate was collected and recrystallised from dimethylformamide/water to afford the title compound as a pale cream solid (0.463 g, 59%). A further recrystallisation from propan-2-ol gave analytically pure material; m.p. 269°–271° C. (from propan-2-ol) (Found: C, 65.92;H, 3.71;N, 7.59. C$_{20}$H$_{13}$ClN$_2$O$_3$ requires C, 65.85;H, 3.71;N, 7.68%); $\delta_H$ (360 MHz, DMSO-d$_6$) 7.03–7.14 (4H, m, ArH), 7.23 (1H, dt, J 2, 8.5 Hz, ArH), 7.32 (1H, d, J 2 Hz, ArH), 7.43 (1H, t, J 8 Hz, 5'-H), 7.85 (1H, m, ArH), 7.94 (1H, d, J 8.7 Hz, 5-H), 8.18 (1H, dd, J 5, 2 Hz, 6"-H), 10.46 (1H, br s, OH), 11.55 (1H, br s, NH); m/z 364 (M$^+$).

The following were prepared in an analogous manner using the appropriate heteroaryl bromide for the Ullman condensation reaction.

EXAMPLE 58

7-Chloro-4-hydroxy-3-[3-(3-thienyloxy)phenyl]-2(1H)-quinolone m.p. >315° C. (dec) (from dimethylformamide/water) (Found: C, 61.57;H, 2.88;N, 3.74. C$_{19}$H$_{12}$ClNO$_3$S requires C, 6;1.71;H, 3.27;N, 3.79%); $\delta_H$ (360 MHz, DMSO-d$_6$) 6.93 (3H, m, ArH), 7.05 (1H, br s, ArH), 7.14 (1H, br d, J 8 Hz, ArH), 7.21 (1H, dd, J 8.6, 2 Hz, 6-H), 7.31 (1H, d, 2 Hz, 8-H), 7.37 (1H, t, J 8 Hz, 5'-H), 7.56 (1H, dd, J 5, 3 Hz, ArH), 7.93(1H, d, J 8.6 Hz, 5-H), 10.37 (1H, br s, OH), 11.52 (1H, br s, NH); m/z 369 (M$^+$).

EXAMPLE 59

7-Chloro-3-[3-(3-furyloxy)phenyl]-4-hydroxy-2(1H)-quinolone m.p. >260° C. (dec) (freeze dried); $\delta_H$ (360 MHz, DMSO-d$_6$) 6.50(1H, m, 4"-H), 6.99 (1H, dd, J 8,2 Hz, 4'-H), 7.08(1H, br s, 2'-H), 7.13 (1H, br d, J 8 Hz, 6'-H), 7.20(1H, dd, J 8.6, 2 Hz, 6-H), 7.30 (1H, d, J 2 Hz, 8-H), 7.36 (1H, t, J 8 Hz, 5'-H), 7.63 (1H, t, J 1.8 Hz, 5"-H), 7.70 (1H, br s, 2"-H), 7.93(1H, d, J 8.6 Hz, 5-H), 10.36 (1H, br s, OH), 11.45 (1H, br s, NH); m/z 353 (M$^+$), (Found: M$^+$, 353.0446. $C_{19}H_{12}ClNO_4$ requires M, 353.0455).

EXAMPLE 60

7-Chloro-4-hydroxy-3-(3-phenylamino)phenyl-2 (1H)-quinolone

To a solution of sodium methoxide (251 mgs, 4.65 mmol) in dry methanol (20 ml) was added a solution of methyl 3-hydroxyphenylacetate (716 mgs, 4.65 mmol) in methanol (5 ml). This was followed by the rapid addition of benzanilino chloride (1g, 4.65 mmol)in ether/methanol (10 ml:2 ml). The reaction was stirred at room temperature overnight. The solvent was evaporated and the residue partitioned between water (20 ml) and dichloromethane (20 ml). The aqueous phase was further extracted with dichloromethane (2×40 ml) and the combined organics dried and evaporated. The residue was chromatographed on silica, eluting with 25% ethyl acetate/60°–80° petrol, to yield N-phenylbenzimino-3-(carbomethoxymethyl)phenyl ether as an oil (1 g); $\delta_H$ (CDCl$_3$) 3.55 (2H, s, C$\underline{H}_2$CO$_2$Me), 3.66 (3H, s, CO$_2$Me), 6.94–6.98 (5H, m, ArH), 7.15–7.19 (5H, m, ArH), 7.35–7.41 (4H, m, ArH).

The foregoing imidate (1 g, 3.1 mmol) in diphenyl ether (20 ml) was heated at 240° for 72 hrs. The reaction was cooled, diluted with acetonitrile (100 ml) and extracted with 60°–80° petrol (5×100 ml). The acetonitrile phase was evaporated and the residue chromatographed on silica, eluting with 25% ethyl acetate/60°–80° petrol, to yield methyl 3-(N-benzoylanilino)phenylacetate as an oil (800mg); $\delta_H$ (CDCl$_3$) 3.54 (2H, s, C$\underline{H}_2$CO$_2$Me), 3.64 (3H, s, CO$_2$Me), 7.04–7.29 (12H, m, ArH), 7.42 (2H, d, J 7.2 Hz, ArH).

The ester (600 mgs, 1.9 mmol) in 4N sodium hydroxide (20 ml) and methanol (20 ml) was stirred at room temperature overnight. The solvent was evaporated and the residue dissolved in water (10 ml) and acidified with 5N hydrochloric acid. The acidic solution was extracted with dichloromethane (3×50 ml), and the combined organics dried and evaporated to afford 3-(N-benzoylanilino)phenylacetic acid as an oil (550 mgs); $\delta_H$ (CDCl$_3$) 3.59 (2H, s, C$\underline{H}_2$CO$_2$H), 6.83–7.29 (10H, m, ArH), 7.42–7.48 (3H, m, ArH), 8.09 (2H, d, J 7.2 Hz, ArH).

The title compound was prepared from the foregoing acetic acid; m.p. 259°–262° C. (from DMF/H$_2$O) (Found: C, 68.51; H, 3.50;N, 7.21; $C_{21}H_{15}ClN_2O_2$ requires C, 69.52;H, 4.16;N, 7.75%); $\delta_H$ (DMSO-d$_6$) 6.77–6.82 (1H, m, ArH), 7.03 (1H, d, J 7.2 Hz, ArH), 7.08–7.11 (2H, m, ArH), 7.19–7.31 (5H, m, ArH), 7.91 (1H, d, J 8.7 Hz, 5-H), 8.15 (1H, s, ArH), 10.21 (1H, br s, OH), 11.52 (1H, br s, NH); m/z 362 (M$^+$).

EXAMPLE 61

7-Chloro-4-hydroxy-3-[3-(2-dimethylaminophenoxy)]- phenyl-2(1H)-quinolone

2-Fluoronitrobenzene (4.2 ml, 40 mmol), methyl 3-hydroxyphenylacetate (5 g, 32.5 mmol) and potassium carbonate (6.9 g, 50 mmol) were heated together in DMF (100 ml) at 100° C. for 36 hrs. After evaporation of the solvent, the residue was partitioned between water (100 ml) and dichloromethane (100 ml), and the aqueous phase further extracted with dichloromethane (2×100 ml). The combined organics were dried and evaporated, and the residue chromatographed on silica, eluting with 25% ethyl acetate/60°–80° petrol to yield methyl 3-(2-nitrophenyloxy)phenylacetate (4 g); $\delta_H$ (CDCl$_3$) 3.62 (2H, s, C$\underline{H}_2$CO$_2$Me), 3.69 (3H, s, CO$_2$Me), 6.94 (1H, d, J 7.2 Hz, ArH), 7.00–7.04 (2H, m, ArH), 7.09 (1H, d, J 8.3 Hz, ArH), 7.19 (1H, t, J 8.3 Hz, ArH), 7.32 (1H, t, J 7.9 Hz, ArH), 7.50 (1H, t, J 7.2 Hz, ArH), 7.94 (1H, d, J 8.2 Hz, ArH).

A solution of the ester (1 g) in ethanol (20 ml) containing formaldehyde (37% in water, 5 ml) was hydrogenated over 10% Pd/C (150 mg) at 50 psi for 5 hrs. After removal of the catalyst and evaporated of the solvent, the residue was chromatographed on silica, eluting with 25% ethyl acetate/ 60°–80° petrol to yield methyl 3-(2-dimethylaminophenoxy)phenyl acetate as an oil (800mg); $\delta_H$ (CDCl$_3$) 2.60 (6H, s, NMe$_2$), 3.58 (2H, s, C$\underline{H}_2$CO$_2$Me), 3.66 (3H, s,CO$_2$Me), 6.62–6.90 (4H, m, ArH), 6.95–7.00 (1H, m, ArH), 7.04–7.11(1H, m, ArH), 7.23 (1H, t, J 7.8 Hz, ArH); m/z 285 (M$^+$).

The ester (1 g) was stirred in a mixture of methanol (20 ml) and 4N sodium hydroxide (20 ml) for 3 hrs. The solvent was evaporated, water (10 ml) added to the residue and the mixture acidified with 5N hydrochloric acid. The acidic solution was extracted with dichloromethane (3×50 ml), and the combined organics dried and evaporated to yield 3-(2-dimethylaminophenoxy)phenylacetic acid (650 mgs); $\delta_H$ (CDCl$_3$) 2.99 (6H, s, NMe$_2$), 3.62 (2H, s C$\underline{H}_2$CO$_2$MH), 6.87–6.95 (4H, m, ArH), 7.03–7.13 (3H, m, ArH), 7.25–7.31 (1H, m, ArH).

The title compound was prepared from the above acetic acid. m.p. 269°–271° C. (from DMF/H$_2$O) (Found: C, 67.98;H, 4.83; N, 6.96; $C_{23}H_{19}ClN_2O_3$ requires C, 67.90;H, 4.71;N, 6.88%); $\delta_H$ (DMSO-d$_6$) 2.75 (6H, s, NMe$_2$), 6,78(1H, dd, J 7.7 and 1.9 Hz, ArH), 6.87–6.94 (3H, m, ArH), 7.00–7.10 (3H, m, ArH), 7.19 (1H, dd, J 8.6 and 2.0 Hz, ArH), 7.29–7.35 (2H, m, ArH), 7.92 (1H, d, J 8.4 Hz, 5-H), 11.48 (1H, br s, NH); m/z 406 (M$^+$).

EXAMPLE 62

7-Chloro-4-hydroxy-3-[3-(4-methoxybenzyl)phenyl]- 2(1H)-quinolone

White amorphous solid, m.p. 282°–284° C. (from dimethylformamide); (Found: C, 70.65;H, 4.28;N, 3.70. $C_{23}H_{18}NO_3Cl$ requires C, 70.50;H, 4.63;N, 3.57%);$\delta$ (360 MHz, DMSO-d$_6$) 3.71 (3H, s, OMe), 3.90 (2H, s, CH$_2$), 6.83 (2H, d,J 7 Hz, ArH, H $\underline{o}$ to OMe), 7.1–7.3 (8H, m, ArH), 7.91(1H, d, J 8.6 Hz, H-5), 10.23 (1H, br s, OH), 11.50 (1H, s, NH); m/z (EI$^+$) 391 ($\underline{M}^+$).

EXAMPLE 63

7-Chloro-4-hydroxy-3-[3-(3-methoxyphenoxyl)- phenyl]-2(1H)-quinolone

To a solution of the potassium salt of 3-hydroxybenzyl alcohol (8.1 g, 50 mmol) in N-methyl pyrolidinone (20 ml) were added 3-bromoanisole (11.22 g, 60 mmol), copper (I) chloride (0.1 g, 1 mmol) and p-hydroxyquinoline (0.1 g, 1 mmol) and the reaction was heated to 170° C. for fifty hours. The reaction was cooled to room temperature, diluted with water (150 ml) and extracted with ether (5×50 ml). The combined extracts were dried (MgSO$_4$) and evaporated. The residue was purified by flash chromatography (eluting with 10% ethyl acetate/60°–80° petrol) to afford 3-(3-methoxyphenoxy)benzyl alcohol as a pale oil 6.0 g (52%); a (CDCl$_3$) 3.80 (3H, s, OC$\underline{H}_3$), 4.64 (2H, s, C$\underline{H}_2$OH), 6.54–6.70 (3H, m, ArH), 6.88–7.10 (3H, m, ArH), 7.18–7.36 (2H, m, ArH).

The alcohol (5.31 g, 23 mmol) was dissolved in dichloromethane (40 ml) and treated with thionyl chloride (2.6 ml, 35 mmol) and dimethylformamide (catalytic 5 drops). The mixture was stirred overnight. The reaction mixture was evaporated in vacuo and azeotroped with toluene (2×10 ml) to give 3-(3-methoxyphenoxy)benzyl chloride as a light brown oil (5.57 g, 97%). The chloride (5.30 g, 21.3 mmol) was dissolved in dimethyl sulphoxide (20 ml), potassium cyanide (1.45 g, 22.4 mmol) was added and the mixture was stirred at room temperature overnight. The reaction was diluted with water (100 ml) and extracted with ether. The combined extracts were dried (MgSO$_4$) and evaporated to give 3-(3-methoxyphenoxy)phenyl acetonitrile as a brown oil (4.04 g, 79%).

The nitrile (4.0 g, 16.7 mmol) was dissolved in ethanol (20 ml), aqueous sodium hydroxide (5M, 7 ml) was added and the mixture was heated at reflux for two hours. The mixture was cooled to room temperature and concentrated in vacuo. The residue was diluted with aqueous sodium hydroxide (1N, 40 ml) and washed with ether (40 ml, 2×20 ml). The aqueous layer was acidified (5N, HCl) and the resultant gum extracted into dichloromethane (3×25 ml). The combined organics were dried (MgSO$_4$) and evaporated to give 3-(3-methoxyphenoxy)phenylacetic acid as a mobile brown oil (2.36 g, 55%). δ (CDCl$_3$) 3.61 (2H, s, C$\underline{H}_2$CO$_2$H), 3.77 (3H, s, OC$\underline{H}_3$), 6.55–6.70 (3H, m, ArH), 6.88–7.02 (3H, m, ArH), 7.14–7.29 (2H, m, ArH); m/z 258 (M$^+$).

The title compound was prepared by procedures analogous to those above.

m.p. 268°–270° C. (from DMF/H$_2$O). (Found: C, 66.81;H, 3.95;N, 3.67. C$_{22}$H$_{16}$ClNO$_4$ requires C, 67.10;H, 4.10;N, 3.56%) δ$_H$ (DMSO-d$_6$) 3.73 (3H, s, OC$\underline{H}_3$), 6.63 (2H, m, ArH), 6.69 (1H, dd, J 7.9 and 2.1 Hz, ArH), 6.94 (1H, dd, J 8.0 and 2.0 Hz, 6-H), 7.0 (1H, s, ArH), 7.15–7.41 (5H, m, ArH), 7.92 (1H, d, J 8.6 Hz, 5-H), 11.37 (1H, s, N$\underline{H}$); m/z 392 (M$^+$).

EXAMPLE 64

7-Chloro-4-hydroxy-3-[3-(2-methoxyphenoxy)-phenyl]2(1H)-quinolone

This was prepared in an analogous manner from 2-bromoanisole.

m.p. 258°–260° C. (from DMF/H$_2$O) (Found: C, 67.05;H, 3.73;N, 3.29. C$_{22}$H$_{16}$NClO$_4$ requires C, 67.10;H, 4.10;N, 3.56%) δ$_H$ (DMSO-d$_6$) 3.73 (3H, s, OC$\underline{H}_3$), 6.75 (1H, dd, J 10.2 and 2.09 Hz, ArH), 6.89 (1H, s, ArH), 6.96 (1H, m, ArH), 7.05 (2H, d, J 7.2 Hz, ArH), 7.17 (3H, m, ArH), 7.30 (2H, m, ArH), 7.92 (1H, d, J 8.7 Hz, 5-H), 11.48 (1H, br s, NH); m/z (CI$^+$, NH$_3$) 394 (M$^+$+H).

EXAMPLE 65

7-Chloro-4-hydroxy-3-[3-(2-methylphenoxy)phenyl]-2(1H)-quinolone

This compound was prepared in an analogous manner from 2-bromotoluene.

m.p. 288°–290° C. (from DMF/H$_2$O) (Found: C, 69.21;H, 3.92;N, 3.99. C$_{22}$H$_{16}$ClNO$_3$.0.15(H$_2$O) requires C, 69.44;H, 4.32;N, 3.68%); δ$_H$ (DMSO-d$_6$) 2.22 (3H, s, C$\underline{H}_3$), 6.84 (1H, dd, J 8.0 and 1.7 Hz, ArH), 6.89 (1H, s, ArH), 6.96 (1H, d, J 8.0 Hz, Ar—H), 7.05–7.10 (2H, m, ArH), 7.18–7.22 (2H, m, ArH), 7.30–7.36 (3H, m, ArH), 7.92 (1H, d, J 8.6 Hz, 5-H), 11.49 (1H, s, N$\underline{H}$); m/z 377 (M$^+$).

EXAMPLE 66

7-Chloro-4-hydroxy-3-(3'-biphenyl)-2(1H)-quinolone m.p.>345° C. (dec) (from DMF/H$_2$O) (Found: C, 71.58;H, 4.17;N, 4.10. C$_{21}$H$_{14}$ClNO$_2$.0.25(H$_2$O) requires C, 71.59;H, 4.15;N, 3.98%) δ$_H$ (DMSO-d$_6$) 7.22 (1H, dd, J 8.6 and 1.9 Hz, 6H), 7.34–7.38 (3H, m, ArH), 7.45–7.52 (3H, m, ArH), 7.60–7.68 (4H, m, ArH), 7.96 (1H, d, J 8.6 Hz, 5-H), 10.39 (1H, br s, O$\underline{H}$), 11.57 (1H, s, N$\underline{H}$); m/z 347 (M$^+$).

EXAMPLE 67

7-Chloro-4-hydroxy-3-(3-phenylthiophenyl)-2(1H)-quinolone

To a solution of 3-bromobenzyaldehyde (14.22 g, 77mmol) in toluene (100 ml) was added paratoluenesulphonic acid (760 mg, 4 mmol) and ethylene glycol (9.5 g, 154 mmol). This mixture was heated at reflux under Dean-Stark conditions for sixteen hours. The reaction was cooled to room temperature and washed with sodium carbonate (2×40 ml) and water (2×40 ml). The organics were dried (MgSO$_4$) and evaporated in vacuo to give 3-bromobenzyaldehyde ethylene glycol acetal as a pale yellow oil (17.5 g, 100%). A solution of the foregoing bromide (5.5 g, 24 mmol) in tetrahydrofuran (80 ml) was cooled to −78° C. (cardice/acetone) and treated with tert butyllithium (48 mmol in pentane), followed by phenydisulphide (5 g, 25 mmol) in THF (40 ml). Once the additions were complete the reaction was stirred at −78° C. for one hour and then allowed to warm to room temperature. After one hour at room temperature the reaction was quenched by the addition of water (150 ml). The mixture was concentrated in vacuo and the residue extracted into ether (5×25 ml). The combined extracts were dried (MgSO$_4$) and evaporated in vacuo. The mixture was purified by flash chromatography (eluting with 10% ethyl acetate/60°–80° petrol) to afford (3-phenylthio)benzaldehyde ethylene glycol acetal as an oil (5.40 g, 87%). To a solution of the foregoing thioether (5.3 g, 20.5 mmol) in tetrahydrofuran was added hydrochloric acid (5M, 8 ml) and the mixture was stirred for fifteen hours. A further portion of acid was added (4 ml) and the stirring continued for a further twenty hours. The mixture was concentrated in vacuo, diluted with water (25 ml) and extracted with dichloromethane (5×25 ml). The combined extracts were washed with sodium carbonate (50 ml), dried (MgSO$_4$) and evaporated in vacuo to give 3-phenylthio benzaldehyde as a yellow oil (4.21 g, 89%). δ$_H$ (CDCl$_3$) 7.25–7.58 (7H, m, ArH), 7.66–7.80 (2H, m, ArH), 9.92 (1H, s, CHO).

The foregoing aldehyde (4.21 g, 18.3 mmol) was dissolved in tetrahydrofuran (40 ml), Triton B (2 ml of a 40% solution in methanol) and methyl methyl thiomethylsulphoxide (4.2 ml, 40.3 mmol) were added and the mixture heated at reflux for sixty five hours. The mixture was cooled to room temperature and concentrated in vacuo. The residue was diluted with dichloromethane (40 ml), washed with water (15 ml), sodium bisulphite (2×15 ml) and water (15 ml) before drying (MgSO$_4$) and evaporation in vacuo. The mixture was purified by flash chromatography (eluting with 25% ethyl acetate/petrol 60°–80°) to afford 1-methylsulphonyl-1-methylthio-2-(3-phenylthio)phenylethylene as a pale oil (4.97 g, 85%). To a solution of the foregoing ethylene (4.9 g, 15.3 mmol) in 1,2-dimethoxy-ethane (40 ml) was added concentrated hydrochloric acid (10 ml) and the mixture was heated at reflux for two hours. The reaction was cooled to room temperature and concentrated in vacuo. The residue was dissolved in aqueous sodium hydroxide (1N, 50 ml) and washed with ether (3×15 ml). The aqueous layer was acidified (5N HCl) and the resultant precipitate extracted into dichloromethane (4×15 ml). The combined organics were dried (MgSO$_4$) and evaporated in vacuo to give 3-phenylthio phenylacetic acid as a pale oil which crystallised on standing (2.29 g, 61%). $\delta_H$ (CDCl$_3$) 3.59 (2H, s, CH$_2$CO$_2$H), 7.14–7.43 (9H, m, ArH).

The title compound was prepared using procedures analogous to those above.

m.p. 291°–293° C. (dec) (from DMF/water) (Found: C, 66.62; H, 3.75;N, 3.96. C$_{21}$H$_{14}$NClO$_2$S requires C, 66.40;H, 3.72;N, 3.69%). $\delta_H$ (DMSO-d$_6$) 7.21 (1H, dd, J 8.6 and 2.0 Hz, 6-H), 7.35 (9H, m, ArH), 7.93 (1H, d, J 8.6 Hz, 5-H), 10.45 (1H, br s, OH), 11.55(1H, s, NH); m/z 379 (M$^+$).

EXAMPLE 68

7-Chloro-4-hydroxy-3-(3-phenylsulphonylphenyl)-2(1H)-quinolone

To a solution of methyl-4-chloro-2-[(3-phenylthio)phenylacetamido]benzoate (5 13mg, 1.25 mmol) (an intermediate from the above example) in dichloromethane (20 ml) was added meta-chloroperoxybenzoic acid (616 mg of a 70% solid, 2.5 mmol) and the mixture was stirred at room temperature for three hours. The reaction was washed with sodium carbonate (25 ml) and the aqueous layer extracted with dichloromethane (3×15 ml). The combined organics were dried (MgSO$_4$) and evaporated in vacuo. The mixture was purified by flash chromatography on silica (eluting with 10% ethyl acetate/60°–80° petrol) to give methyl 4-chloro-2-[(3-phenylsulphonyl)phenylacetamido]benzoate as a white solid (532 mg, 96%). $\delta_H$ (CDCl$_3$) 3.73 (2H, s, CH$_2$Ph), 3.76 (3H, s, CO$_2$Me), 7.03 (1H, dd, J 8.4 and 2.1 Hz, 5-H), 7.19–7.37 (9H, m, ArH), 7.90 (1H, d, J 8.6 Hz, 6-H), 8.79 (1H, d, J 2.1 Hz, 3-H).

The amide was cyclised to give the title compound, m.p. 260° C. slow decomp (from DMF/water) (Found: C, 61.54;H, 3.53; N, 3.80. C$_{21}$H$_{14}$NClO$_4$ S requires C, 61.24;H, 3.43;N, 3.40%). $\delta_H$ (DMSO-d$_6$) 7.24 (1H, dd, J 8.6 and 2.0 Hz, 6-H), 7.34 (1H, d, J 2.0 Hz, 8-H), 7.60–7.72 ($\delta_H$, m, ArH), 7.88 (1H, m, ArH), 7.96–7.99 (4H, m, ArH), 10.74 (1H, vbr s, OH), 11.63(1H, s, NH); m/z 411 (M$^+$).

EXAMPLE 69

3-(3-Benzoylamino)phenyl-7-chloro-4-hydroxy-2(1H)-quinolone

A suspension of platinum oxide (0.35 g) in ethyl acetate (100 ml) containing methyl 4-chloro-2-(3-nitrophenyl)acetamidobenzoate (9.96 g, 28.6 mmol) was shaken under an atmosphere of hydrogen at 40 psi until hydrogen uptake had ceased. The suspension was filtered and the filtrate evaporated to leave methyl 2-(3-aminophenyl)acetamido-4-chlorobenzoate as a pale green solid (9.22 g); $\delta$ (CDCl$_3$) 3.65 (2H, s, CH$_2$), 3.66 (3H, s, OCH$_3$), 6.61 (1H, dd, J 7.9 and 2.1 Hz, ArH), 6.70 (1H, s, ArH), 6.74 (1H, d, J 7.6 Hz, ArH), 7.01(1H, dd, J 8.6 and 2.0 Hz, 5-H), 7.14(1H, d, J 7.7 Hz, ArH), 7.89(1H, d, J 8.6 Hz, 6-H), 8.81 (1H, d, J 2.0 Hz, 3-H) and 11.03 (1H, br s, CONH).

A sample of the aforementioned amine (900 mg, 2.8 mmol) was stirred for 5h with benzoyl chloride (4.23 mg, 3 mmol) in dichloromethane (20 ml) containing pyridine (1 ml). The mixture was washed with HCl (1M, 15ml), dried (MgSO$_4$), filtered and the filtrate evaporated to leave a solid which was recrystallised from methanol to afford methyl 2-(3-benzoylamino)acetamido-4-chlorobenzoate (901 mg) as a colourless solid; m.p. 156°–157° C.

Cyclisation as before afforded the title compound as a buff solid; m.p. 310°–312° C. (from DMF/water) (Found: C, 67.88;H, 3.62;N, 7.08. C$_{22}$H$_{15}$ClN$_2$O$_3$ requires: C, 67.61;H, 3.87;N, 7.17%); $\delta_H$ (DMSO-d$_6$) 7.09 (1H, d, J 7.7 Hz, 6'-H), 7.21 (1H, dd, J 9.0 and 2.0 Hz, 4'-H), 7.32 (1H, d, J 2.0 Hz, 2'-H), 7.37 (1H, t, J 7.8 Hz, 5'-H), 7.50–7.61 (3H, m, ArH), 7.78–7.81 (2H, m, ArH), 7.93–7.78 (3H, m, ArH), 10.26 (1H, br s, NHCOPh), and 11.53 (1H, br s, NHCO); m/z 391 (M$^+$).

EXAMPLE 70

3(3-N-Benzylamino)phenyl-7-chloro-4-hydroxy-2(1H)-quinolone

A solution of methyl 2-(3-aminophenylacetamido)-4-chloro-benzoate (1.80 g, 5.6 mmol) and benzaldehyde (0.62 g, 5.8 mmol) in toluene (60 ml) containing a trace of p-toluenesulphonic acid was stirred under reflux under a Dean and Stark trap for 50 min. On cooling the solvent was removed by evaporation, the residue dissolved in THF (15 ml) and a solution of potassium hexamethyldilisilazide in toluene (0.5M, 25 ml) added. After stirring for 1.5h, sufficient methanol was added to the suspension to give complete dissolution of the precipitate and the resulting solution evaporated to leave a yellow solid. This was redissolved in methanol (50 ml) and excess acetic acid added. After standing for 0.5 h, the precipitated solid was collected, washed with methanol, and dried to afford the corresponding imine as a buff powder (1.81 g).

A sample (300 mg, 0.8 mmol) was dissolved in a mixture of acetic add (10 ml) and DMF (5 ml) and sodium cyanoborohydride (150 mg, 2.4 mmol) added. After stirring for 1.5 h, the solution was evaporated and the residue dissolved in dilute aqueous sodium hydroxide and containing some methanol. Addition of 10% aqueous citric acid gave a precipitate which was collected and crystallised to afford the title compound as buff plates; m.p. 259°–260° C. (from DMF/water) (Found: C, 70.20;H, 4.35;N, 7.22. C$_{22}$H$_{17}$ClN$_2$O$_2$ requires: C, 70.12;H, 4.55;N, 7.43%); $\delta_H$(DMSO-d$_6$) 4.27 (2H, d, J 4.5 Hz, —NHCH$_2$Ph), 6.16 (1H, t, J 5.9 Hz, —NHCH$_2$Ph), 6.50 (2H, dd, J 7.7 and 1.7 Hz, ArH), 6.62 (1H, s, 2'-H), 7.06 (1H, t, J 7.7 Hz, ArH), 7.17–7.24 (2H, m, ArH), 7.28–7.39 (5H, m, ArH), 7.88(1H, d, J 8.7 Hz, ArH), 10.00(1H, br s, OH) and 11.44 (1H, br s, NH); m/z 377 (M$^+$).

EXAMPLE 71

3-(3'-Allyloxyphenyl)-7-chloro-4-hydroxy-2(1H)-quinolone

M.p. >300° C. (from DMF/water) (Found: C, 65.63;H, 4.32; N, 4.08. C$_{18}$H$_{14}$ClNO$_3$ requires: C, 65.96;H, 4.31;N, 4.27%); $\delta_H$ (DMSO-d$_6$) 4.56 (2H, d, J 5.2 Hz, OCH$_2$CH:CH$_2$), 5.26(1H, dd, J 10.5 and 2.1 Hz, OCH$_2$CH:CH$_2$), 5.42 (1H, dd, J 17.3 and 2.1 Hz, OCH$_2$CH:CH$_2$), 6.06 (1H, m, OCH$_2$CH:CH$_2$), 6.90–6.94 (3H, m, ArH), 7.20 (1H, dd, J 8.6 and 2.0 Hz, 6-H), 7.28–7.31 (2H, m, ArH and 8-H), 7.92 (1H, d, J 8.6 Hz, 5-H), 10.22 (1H, br s, OH), and 11.51 (1H, br s, NH).

EXAMPLE 72

7-Chloro-4-hydroxy-3-(3-(2-methylprop-2-enyloxy))-phenyl-2(1H)-quinolone

M.p. 297°–299° C. (from DMF/water) (Found: C, 66.58;H, 4.88;N, 4.15. $C_{19}H_{16}ClNO_3$ requires: C, 66.77;H, 4.72;N, 4.10%); $\delta_H$ (DMSO-$d_6$) 1.23 (3H, s, CH$_3$), 4.40 (2H, s, OCH$_2$), 4.96 (1H, s, C:CH$_2$), 5.08(1H, s, C:CH$_2$), 6.70–6.94 (3H, m, ArH), 7.20 (1H, dd, J 8.6 and 1.9 Hz, 6-H), 7.27–7.31 (2H, m, ArH) and 8-H), 7.92 (1H, d, J 8.6 Hz, 5-H) and 11.50 (1H, br s, NH); m/z 342 (M$^+$).

EXAMPLE 73

4-Hydroxy-7-methyl-3-(3-phenoxyphenyl)-(1H)-quinolone m.p. 299.3°–300.5° C. (from DMF/H$_2$O) (Found: C, 76.66;H, 4.79;N, 4.01; $C_{22}H_{17}NO_3$ requires C, 76.95;H, 4.99;N, 4.08%); δ (DMSO-$d_6$) 2.37 (3H, s, CH$_3$), 6.94–7.42 (11H, m, 6H, 8H and 9 ×ArH), 7.83 (1H, d, J 8.6 Hz, 5-H), 10.10 (1H, bs, OH), 11.36 (1H, s, NH); m/z 344 (M+1).

EXAMPLE 74

7-Chloro-4-hydroxy-3-(3,4-dimethoxyphenyl)-2(1H)-quinolone m.p. 312°–314° C. (from DMF/H$_2$O); $\delta_H$ (360 MHz, DMSO-$d_6$) 3.74 (3H, s, OCH$_3$), 3.79 (3H, s, OCH$_3$), 6.87–7.00 (3H, m, ArH), 7.19 (1H, d, J 8.6 Hz, 6-H), 7.31 (1H, s, 8-H), 7.90(1H, d, J 8.6 Hz, 5-H), 11.48 (1H, br s, NH); m/z 331 (M$^+$) (Found: m/z 331.0613; $C_{17}H_{14}ClNO_4$ requires 331.0611).

EXAMPLE 75

7-Chloro-3-(4-ethoxyphenyl)-4-hydroxy-2(1H)-quinolone m.p. >320° C. (from DMF/H$_2$O) (Found: C, 64.60%; H, 4.35%; N, 4.32%; C17H$_{16}$ClNO$_3$ requires C, 64.67%; H, 4.47%; N, 4.44%); $\delta_H$ (360 MHz, DMSO-$d_6$) 1.35 (3H, t, J 6.9 Hz, CH$_2$CH$_3$), 4.05 (2H, q, J 6.9 Hz, CH$_2$CH$_3$), 6.92 (2H, d, J 8.7 Hz, 2'-H. 6'-H), 7.17(1H, dd, J 8.6 Hz and 2.0 Hz, 6-H), 7.28(1H, s, 8H), 7.30 (1H, dd, j 8.6 Hz and 2.0 Hz, 3'-H, 5'-H), 7.90(1H, d, J 8.7 Hz, 5-H), 11.39 (1H, br s, NH); m/z 315 (M$^+$).

EXAMPLE 76

7-Chloro-4-hydroxy-3-(4-methoxyphenoxy)phenyl-2(1H)-quinolone m.p. 291°–293° C. (from DMF/H$_2$O) (Found: C, 66.04%; H, 4.43%; N, 3.45%; Cl, 9.17%; $C_{22}H_{16}ClNO_4$,0.25H$_2$O requires C, 66.33%; H, 4.17%; N, 3.52%; Cl, 8.90%); $\delta_H$ (DMSO-$d_6$) 3.74 (3H, s, OCH$_3$), 6.86–6.98 (7H, m, ArH), 7.03–7.08 (3H, m, ArH, 6H), 7.20 (1H, dd, J 8.6 Hz and 2.0 Hz, ArH), 7.30(1H, br s, 8-H), 7.36(1H, t, J 7.89 Hz, ArH), 7.92(1H, d, J 8.6 Hz, 5-H), 11.52 (1H, br s, NH); m/z 393 (M$^+$).

EXAMPLE 77

7-Chloro-4-hydroxy-3-(4-methylphenoxy)phenyl-2(1H)-quinolone m.p. 296°–298° C. (from DMF/H$_2$O) (Found: C, 69.37%; H, 4.45%; N, 3.52%; $C_{22}H_{16}ClNO_3$, 0.15H$_2$O requires C, 69.44%, H, 4.32%; N, 3.68%); $\delta_H$ (DMSO-$d_6$) 2.28 (3H, s, CH$_3$), 6.90–6.99 (4H, m, ArH), 7.11 (1H, d, J 6.6 Hz, 6-H), 7.17–7.22 (3H, m, ArH), 7.31 (1H, s, 8-H), 7.38 (1H, t, J 7.9 Hz, ArH), 7.92 (1H, d, J 8.6 Hz, 5-H), 11.53 (1H, br s, NH); m/z 376 (M$^+$).

EXAMPLE 78

Tablet Preparation

Tablets containing 1.0, 2.0, 25.0, 26.0, 50.0 and 100.0 mg, respectively of the following compounds are prepared as illustrated below:

7-Chloro-4-hydroxy-3-(3-phenoxyphenyl)-2(1H)-quinolone

7-Chloro-4-hydroxy-3-[3-(4-methoxymethoxybenzyl)phenyl]-2(1H)-quinolone

7-Chloro-4-hydroxy-3-[3-(4-methoxybenzyl)phenyl]-2(1H)-quinolone

7-Chloro-4-hydroxy-3-[3-(2-propenyloxy)phenyl]-2(1H)-quinolone

| TABLE FOR DOSES CONTAINING FROM 1–25MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

What is claimed is:

1. A method for the treatment and/or prevention of conditions which require the administration of a selective non-competitive antagonist of NMDA receptors which comprises administering to a patient in need of such treatment an effective amount of a compound of formula I or a pharmaceutically acceptable salt thereof or a prodrug thereof:

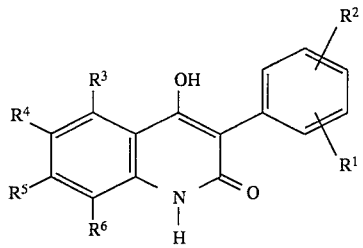

wherein
- $R^1$ and $R^2$ are independently selected from the group consisting of hydrogen, a heterocyclic group selected from the group consisting of $C_{3-7}$heterocycloalkyl, $C_{3-7}$heterocycloalkyl($C_{1-6}$)alkyl, heteroaryl and heteroaryl($C_{1-6}$)alkyl, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ and —$CONR^aR^b$, with the proviso that both $R^1$ and $R^2$ are not simultaneously hydrogen; or $R^1$ and $R^2$ together represent the residue of a heterocyclic ring, selected from the group consisting of dioxolane, dioxane, pyridine, furan, thiophene, pyrrole, thiazole and thiadiazole;
- $R^3$, $R^4$, $R^5$ and $R^6$ are independently selected from the group consisting of hydrogen, hydrocarbon, a heterocyclic group, as defined above, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ and —$CONR^aR^b$; and
- $R^a$ and $R^b$ independently represent hydrogen or a heterocyclic group, as defined above, with the proviso that both $R^a$ and $R^b$ are not simultaneously hydrogen; provided also that when $R^1$ or $R^2$ represents —$OR^a$, —$SR^a$, —$SOR^a$, —$SO_2R^a$, —$COR^a$, or —$CO_2R^a$, then $R^a$ is not hydrogen.

2. The method of claim 1 wherein said $C_{3-7}$heterocycloalkyl group is selected from the group consisting of piperidyl, piperazinyl and morpholinyl.

3. The method of claim 1 wherein said heteroaryl group is selected from the group consisting of pyridyl, quinolyl, isoquinolyl, pyradazinyl, pyrimidinyl, pyrazinyl, pyrrolyl, indoyl, pyranyl, furyl, benzofuryl, thienyl, benzthienyl, imidazolyl, oxadiazolyl and thiadiazolyl.

4. A method for the treatment and/or prevention of conditions which require the administration of an antagonist of AMPA receptors, including schizophrenia, which comprises administering to a patient in need of such treatment an effective amount of a compound of formula I as defined in claim 1 or a pharmaceutically acceptable salt thereof or a prodrug thereof.

5. A pharmaceutical composition comprising an effective amount of a compound of formula IA or a pharmaceutically acceptable salt thereof or a prodrug thereof:

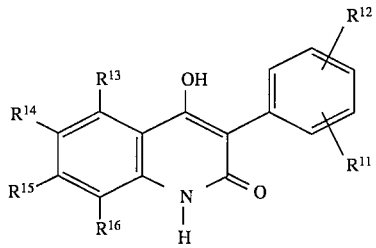

wherein
- $R^{11}$ and $R^{12}$ are independently selected from the group consisting of hydrogen, a heterocyclic group, as defined in claim 10, —$OR^a$, —$SR^a$, —$SOR^a$, —$SO_2R^a$, $SO_2NR^aR^b$, —$NR^aR^b$, —$NR^aCOR^b$, —$NR^aCO_2R^b$, —$COR^a$, —$CO_2R^a$ and —$CONR^aR^b$, with the proviso that both $R^{11}$ and $R^{12}$ are not simultaneously hydrogen; or $R^{11}$ and $R^{12}$ together represent the residue of a heterocyclic ring, as defined above;
- $R^{13}$, $R^{14}$ $R^{15}$ and $R^{16}$ are independently selected from the group consisting of hydrogen, hydrocarbon, a heterocyclic group, as defined above, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ and —$CONR^aR^b$; and
- $R^a$ and $R^b$ independently represent hydrogen or a heterocyclic group, as defined above, with the proviso that both $R^a$ and $R^b$ are not simultaneously hydrogen, provided also that when $R^1$ or $R^2$ represents —$OR^a$, —$SR^a$, —$SOR^a$, —$SO_2R^a$, —$COR^a$, or —$CO_2R^a$, then $R^a$ is not hydrogen; in association with one or more pharmaceutically acceptable carriers and/or excipients.

6. A compound of formula IB or a pharmaceutically acceptable salt or prodrug thereof:

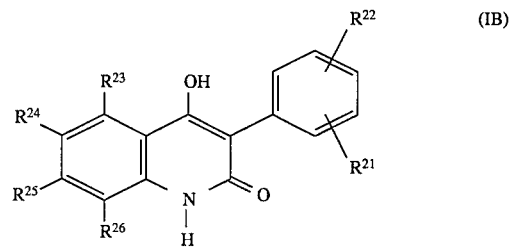

wherein
- $R^{21}$ and $R^{22}$ are independently selected from the group consisting of hydrogen, a heterocyclic group, selected from the group consisting of $C_{3-7}$heterocycloalkyl, $C_{3-7}$ heterocycloalkyl($C_{1-6}$)alkyl, heteroaryl and heteroaryl($C_{1-6}$)alkyl, —$OR^a$, —$SR^a$, —$SOR^a$, —$SO_2R^a$, —$SO_2NR^aR^b$, —$NR^aR^b$, —$NR^aCOR^b$, —$NR^aCOR_2R^b$, —$COR^a$, —$CO_2R^a$ and —$CONR^aR^b$, with the proviso that both $R^{21}$ and $R^{22}$ are not simultaneously hydrogen; or $R^{21}$ and $R^{22}$ together represent the residue of a heterocyclic ring, selected from the group consisting of dioxolane, dioxane, pyridine, furan, thiophene, pyrrole, thiazole and thiadiazole;
- $R^{23}$, $R^{24}$, $R^{25}$ and $R^{26}$ are independently selected from the group consisting of hydrogen, hydrocarbon, a heterocyclic group, as defined above, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ and —$CONR^aR^b$; and
- $R^a$ and $R^b$ independently represent hydrogen or a heterocyclic group, as defined above, with the proviso that both $R^a$ and $R^b$ are not simultaneously hydrogen; provided also that when $R^1$ $R^2$ represents —$OR^a$, —$SR^a$, $SOR^a$, —$SO_2R^a$, —$COR^a$, or —$CO_2R^a$, then $R^a$ is not hydrogen.

7. A compound of formula IIA or a pharmaceutically acceptable salt or prodrug thereof:

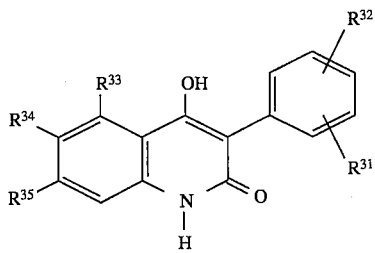

(IIA)

wherein $R^{31}$ and $R^{32}$ are independently selected from the group consisting of hydrogen, heteroaryl($C_{1-6}$)alkyl, heteroaryloxy and heteroarylcarbonyl, wherein heteroaryl is defined above in claim 12, with the proviso that both $R^{31}$ and $R^{32}$ are not simultaneously hydrogen; any of which groups can be optionally substituted or $R^{31}$ and $R^{32}$ together represent the residue of a heterocyclic ring, as defined above;

$R^{33}$ and $R^{35}$ are independently selected from the group consisting of halogen, cyano, trifluoromethyl, nitro, hydroxy, amino, carboxy, $C_{1-6}$alkyl, $C_{2-6}$alkenyl, $C_{1-6}$alkoxy, $C_{1-6}$alkylthio and $C_{2-7}$alkoxycarbonyl; and $R^{34}$ represents hydrogen or halogen.

8. A compound represented by formula IIB and pharmaceutically acceptable salts and prodrugs thereof:

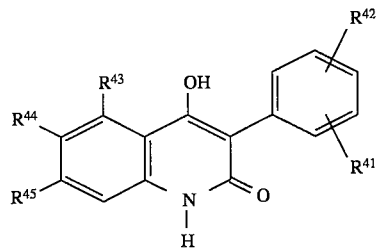

(IIB)

wherein $R^{41}$ is selected from the group consisting of heteroaryl($C_{1-6}$)alkyl, heteroaryloxy, heteroarylcarbonyl, wherein heteroaryl is defined in claim 12, any of which groups can be optionally substituted; and $R^{42}$ is selected from the group consisting of hydrogen, heteroaryl($C_{1-6}$)alkyl, heteroaryloxy, heteroarylcarbonyl, any of which groups can be optionally substituted; or $R^{41}$ and $R^{42}$ together represent the residue of a heterocyclic ring;

$R^{43}$ and $R^{44}$ are independently selected from the group consisting of hydrogen, halogen, cyano, trifluoromethyl, nitro, hydroxy, amino, carboxy, $C_{1-6}$alkyl, $C_{2-6}$alkenyl, $C_{1-6}$alkoxy, $C_{1-6}$alkylthio and $C_{2-7}$alkoxycarbonyl; and $R^{45}$ is independently selected from the group consisting of hydrogen, halogen, cyano, trifluoromethyl, nitro, hydroxy, amino, carboxy, $C_{1-6}$alkyl, $C_{2-6}$alkenyl, $C_{1-6}$alkylthio and $C_{2-7}$alkoxycarbonyl.

9. A compound according to claim 8 represented by formula II C and pharmaceutically acceptable salts and prodrugs thereof:

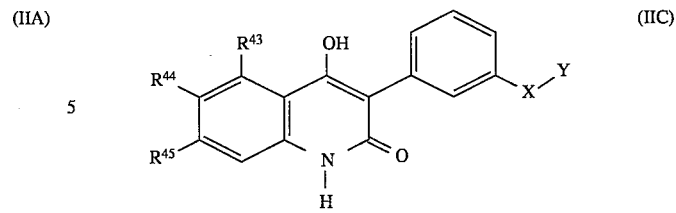

(IIC)

wherein $R^{43}$, $R^{44}$ and $R^{45}$ are as defined in claim 17;

X is selected from the moieties of formula —$CH_2$—, —O— and —CO—; and

Y represents a group of formula (ii), (iii) or (iv):

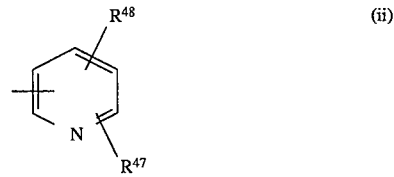

(ii)

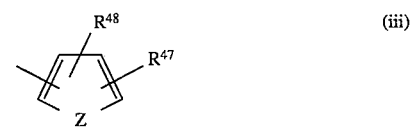

(iii)

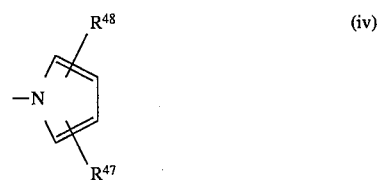

(iv)

in which Z represents oxygen, sulphur or NH; and $R^{47}$ and $R^{48}$ are independently selected from the group consisting of hydrogen, $C_{1-6}$alkyl, morpholinyl($C_{1-6}$)alkyl, hydroxy, $C_{1-6}$alkoxy, $C_{1-6}$alkoxy($C_{1-6}$)alkyl, $C_{1-6}$alkoxy $C_{1-6}$alkoxy, $C_{1-6}$alkylthio and di($C_{1-6}$)alkylamino; and wherein for (ii), (iii), (iv), $R^{47}$ and $R^{48}$ together can represent the residue of a benzene ring.

10. A compound selected from:

7-chloro-4-hydroxy-3-[3-(3-furylcarbonyl)phenyl]-2(1H)-quinolone;

7-chloro-4-hydroxy-3-[3-(3-thienylcarbonyl)phenyl]-2(1H)-quinolone;

7-chloro-4-hydroxy- 3-[3-(1-indolylmethyl)phenyl]-2(1H)-quinolone:

7-chloro-4-hydroxy-3-[3-(1-pyrrolylmethyl)phenyl]-2(1H)-quinolone;

7-chloro-4-hydroxy-3- [3-(3- thienylmethyl)phenyl]-2(1H)-quinolone;

7-chloro-4-hydroxy-3-[3-[3-(indolemethyl)phenyl]-]-2(1H)-quinolone;

7-chloro-4-hydroxy- 3-[3-(2-pyridyloxy)phenyl]-2(1H)-quinolone;

7-chloro-4-hydroxy-3-[3-(3-thienyloxy)phenyl]-2(1H)-quinolone;

7-chloro-4-hydroxy-3-[3-(3-furyloxy)phenyl]-2(1H)-quinolone; and pharmaceutically acceptable salts and prodrugs thereof.

11. The compound of claim 10 being 7-chloro-4-hydroxy-3-[3-(3-thienylcarbonyl)phenyl]-2(1H)-quinolone.

12. A pharmaceutical composition comprising an effective amount of the compound of claim 11 in association with one or more pharmaceutically acceptable carriers and/or excipients.

13. A method for the treatment and/or prevention of schizophrenia which comprises administering to a patient in need of such treatment an effective amount of the compound of claim 11 or a pharmaceutically acceptable salt thereof.

* * * * *